US011377259B1

United States Patent
Kriesel et al.

(10) Patent No.: US 11,377,259 B1
(45) Date of Patent: *Jul. 5, 2022

(54) PROTECTIVE ARTICLES COMPRISING AN ADHESIVE AND COHESIVE THERMOSET VISCOELASTIC POLYMER

(71) Applicant: Universal Tech Corporation, Ettrick, WI (US)

(72) Inventors: Matthew Wayne Kriesel, Melrose, WI (US); Troy Bradley Goodenough, Mindoro, WI (US)

(73) Assignee: Universal Tech Corporation, Ettrick, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/280,849

(22) Filed: Feb. 20, 2019

Related U.S. Application Data

(63) Continuation-in-part of application No. 15/731,815, filed on Aug. 7, 2017, now Pat. No. 11,124,596, which is a continuation-in-part of application No. 14/999,722, filed on Jun. 20, 2016, now Pat. No. 10,807,767.

(60) Provisional application No. 62/231,004, filed on Jun. 22, 2015.

(51) Int. Cl.
| | | |
|---|---|---|
| *B65D 25/04* | (2006.01) | |
| *A61B 50/33* | (2016.01) | |
| *B65D 33/06* | (2006.01) | |
| *B05D 1/02* | (2006.01) | |
| *A01K 97/06* | (2006.01) | |
| *C08G 18/48* | (2006.01) | |
| *C08G 18/36* | (2006.01) | |
| *C08G 18/10* | (2006.01) | |
| *A61B 50/00* | (2016.01) | |
| *A61B 50/30* | (2016.01) | |

(52) U.S. Cl.
CPC .............. *B65D 25/04* (2013.01); *A01K 97/06* (2013.01); *A61B 50/33* (2016.02); *B05D 1/02* (2013.01); *B65D 33/06* (2013.01); *A61B 2050/002* (2016.02); *A61B 2050/3008* (2016.02); *C08G 18/10* (2013.01); *C08G 18/36* (2013.01); *C08G 18/4825* (2013.01); *C08G 18/4829* (2013.01)

(58) Field of Classification Search
CPC ........ B65D 25/04; B65D 33/06; A01K 97/06; B05D 1/02; A61B 50/33; A61B 2050/3008; A61B 250/002; A61B 2050/002; C08G 18/36; C08G 18/10; C08G 18/4829; C08G 18/4825
See application file for complete search history.

(56) References Cited

U.S. PATENT DOCUMENTS

| | | | |
|---|---|---|---|
| 3,507,071 | A | 4/1970 | Bryson |
| 5,677,413 | A | 10/1997 | Barksby et al. |
| 5,864,001 | A | 1/1999 | Masse et al. |
| 6,588,511 | B1 | 7/2003 | Kriesel et al. |
| 6,673,409 | B1 | 1/2004 | Wheatley |
| 6,896,065 | B2 | 5/2005 | Kriesel et al. |
| 7,041,719 | B2 | 5/2006 | Kriesel et al. |
| 7,125,602 | B2 | 10/2006 | Wheatley |
| 7,252,867 | B2 | 8/2007 | Wheatley |
| 7,910,188 | B2 | 3/2011 | Wheatley |
| 7,923,088 | B2 | 4/2011 | Wheatley |
| 8,110,269 | B2 | 2/2012 | Wheatley |
| 8,110,270 | B2 | 2/2012 | Wheatley |
| 8,302,213 | B2 | 11/2012 | Kriesel |
| 9,974,342 | B1 * | 5/2018 | Kriesel .............. A41D 13/0512 |
| D880,950 | S | 4/2020 | Kriesel et al. |
| 10,681,830 | B1 | 6/2020 | Goodenough |
| 10,717,582 | B1 | 7/2020 | Goodenough |
| 10,807,767 | B1 * | 10/2020 | Kriesel ................. B65D 25/04 |
| D902,584 | S | 11/2020 | Kriesel et al. |
| 2004/0191446 | A1 | 9/2004 | Kriesel |
| 2004/0200623 | A1 | 10/2004 | Kriesel |
| 2006/0272367 | A1 | 12/2006 | Kriesel |
| 2006/0287147 | A1 | 12/2006 | Kriesel |
| 2008/0005929 | A1 | 1/2008 | Hardy et al. |
| 2008/0026658 | A1 | 1/2008 | Kriesel |
| 2008/0250729 | A1 | 10/2008 | Kriesel |
| 2009/0042676 | A1 | 2/2009 | Kriesel |
| 2010/0170139 | A1 | 7/2010 | Zhou |
| 2012/0222457 | A1 | 9/2012 | Kriesel et al. |
| 2013/0288060 | A1 | 10/2013 | Pind et al. |
| 2013/0296449 | A1 | 11/2013 | Peterson et al. |
| 2015/0053583 | A1 | 2/2015 | McCormick et al. |

* cited by examiner

*Primary Examiner* — Rabon A Sergent
(74) *Attorney, Agent, or Firm* — Bryan R. Rosiejka

(57) ABSTRACT

A viscoelastic material comprises a unique adhesive and cohesive thermoset viscoelastic polymer coated onto a flexible substrate. The polymer can be formed by curing an uncured polymer mix derived from a thermosetting reaction media of a carefully balanced ratio of isocyanate prepolymer, polyether diols, polyether triols and organic plasticizers. The viscoelastic material can exhibit viscoelastic, adhesive, cohesive, releasability, cleansability and antimicrobial properties. In some aspects, the viscoelastic material can be fabricated into a personal protective article. In one embodiment, the personal protective article is a footwear cover.

31 Claims, 10 Drawing Sheets

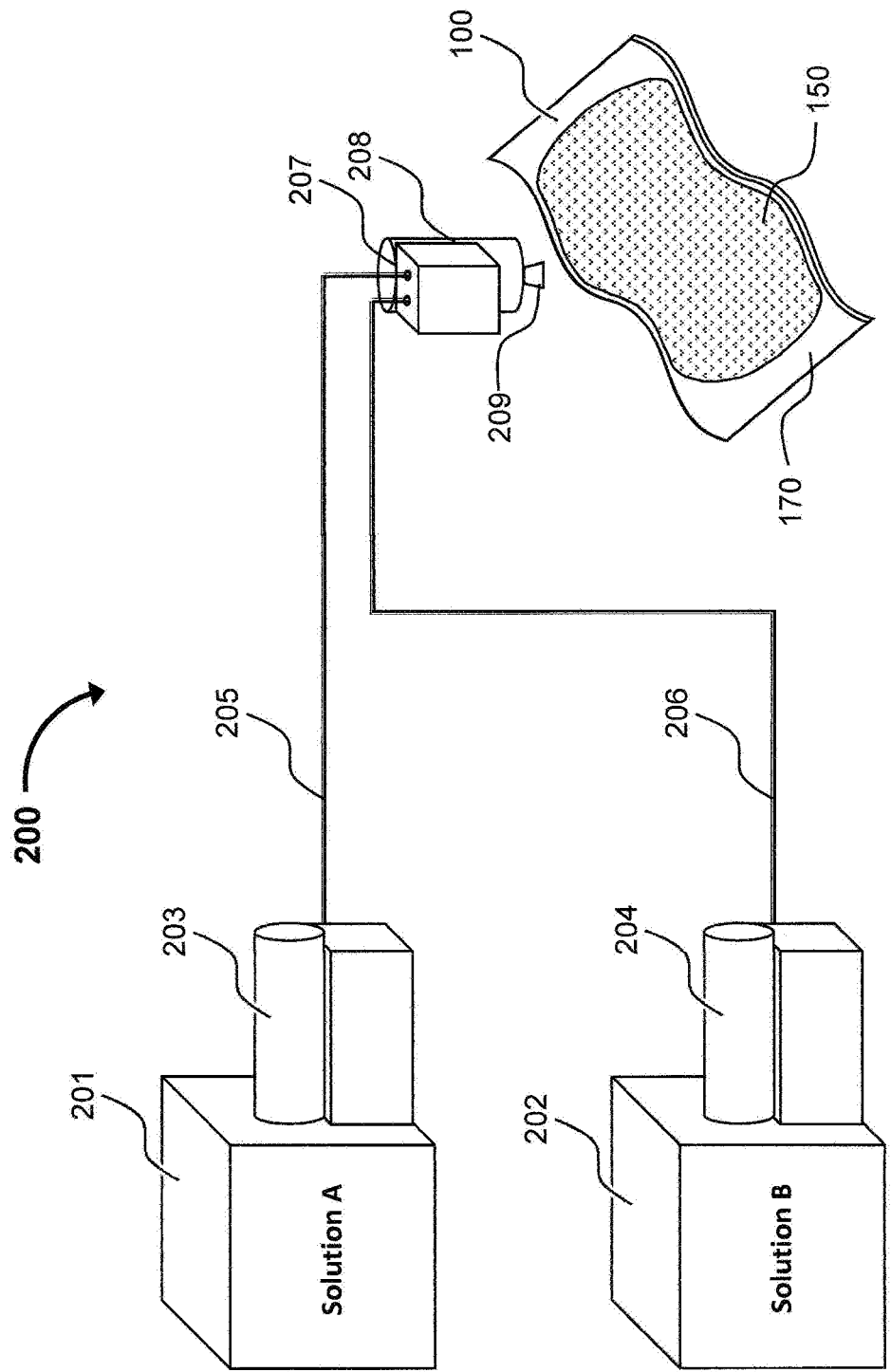

PROTECTIVE ARTICLES COMPRISING AN ADHESIVE AND COHESIVE THERMOSET VISCOELASTIC POLYMER

CROSS-REFERENCE TO RELATED APPLICATIONS

This application is a Continuation-in-Part of, and claims priority to, U.S. patent application Ser. No. 15/731,815 filed in the United States Patent and Trademark Office on Aug. 7, 2017, which is a Continuation-in-Part of U.S. patent application Ser. No. 14/999,722 filed in the United States Patent and Trademark Office on Jun. 20, 2016, which is a Nonprovisional application of Provisional U.S. Patent Application No. 62/231,004 filed in the United States Patent and Trademark Office on Jun. 22, 2015, all of which applications are hereby incorporated in their entirety herein in a manner that is consistent herewith.

TECHNICAL FIELD

The present disclosure relates to flexible substrates having adhesive and cohesive viscoelastic properties. In some more particular embodiments, the present invention relates to personal protective articles comprising such substrates.

BACKGROUND

The present invention relates to viscoelastic materials comprising flexible substrates coated with a unique adhesive and cohesive thermoset viscoelastic polymer. In some aspects, the viscoelastic materials can exhibit adhesive, cohesive, releasability, cleansability and/or antimicrobial properties.

Flexible substrates can comprise many different materials including, but not limited to, nonwoven fabrics (e.g., spunbond polypropylene, nonwoven laminates (such as spunbond/meltblown/spunbond laminates), etc.), woven fabrics (e.g., textiles, etc.), rubbers, nitrile, foams, leather, plastics, and the like, or combinations thereof. Such flexible substrates can be utilized for various uses on their own, or can be used in the fabrication of articles, such as personal protective articles. As is generally known, personal protective articles, such as footwear covers, surgical gowns, surgical drapes, gloves, hats, facemasks, coveralls, body suits, mats, pads, aprons, and the like, have been designed to greatly reduce or prevent the transmission of solid/particulate contaminants, liquid contaminants, and/or airborne contaminants through such articles. For example, solid or particulate contaminants can include dirt, debris, salts, textile particles, mineral fines, skin squamae, hairs, solid chemicals, and the like. Examples of liquid sources can include human liquids (e.g., perspiration, blood, plasma, etc.), saline, oils, liquid chemicals, and the like. Examples of airborne contaminants can include biological contaminants (e.g., bacteria, viruses, germs, fungal spores, etc.), dust, lint, and the like. In addition, personal protective articles can provide properties, such as grip or adhesiveness to the user, with respect to surfaces upon which the articles come into contact.

It has been observed herein that in many instances, currently available personal protective articles fashioned from flexible substrates fail to provide certain desired properties sufficiently, such as adhesiveness, cohesiveness, releasability, cleansability, and/or antimicrobial properties. Thus, there is a need for materials comprising flexible substrates, or personal protective articles derived therefrom, which can provide improved adhesiveness, cohesiveness, releasability, cleansability, and/or antimicrobial properties.

In addition, it is not uncommon for the surfaces of objects or the surrounding environment to become contaminated with small amounts of solid/particulate, liquid, and/or airborne contaminants. In the case where such surfaces are relatively smooth or slippery, for example, existing flexible substrates, or personal protective articles derived therefrom, are often coated with a traction enhancing substance (e.g., hot melts or amorphous atactic olefin polymers (such as, polypropylene, polyethylene, and copolymers of propylene and ethylene)) which increases the coefficient of friction to provide slip-resistant properties. Unfortunately, while current traction enhancing coatings tend to marginally increase the coefficient of friction with respect to such smooth or slippery surfaces (as compared to uncoated protective articles), it has been discovered herein that the resulting increase in coefficient of friction remains insufficient, resulting in periodic slippage despite the presence of such currently available coatings. Thus, there is a need for materials comprising flexible substrates, or personal protective articles derived therefrom, comprising a coating which further improves the coefficient of friction over currently available friction enhancing coatings. There is also a need for materials comprising flexible substrates, or personal protective articles derived therefrom, possessing a preselected degree of effective adhesiveness coupled with highly desirable cohesiveness and releasability attributes.

Furthermore, currently available traction enhancing coatings typically do not additionally exhibit a tackiness (i.e., adhesiveness) sufficient to not only strengthen the grip of the user to a particular surface, but also to sufficiently attract and retain contaminants to effectively maintain or improve the condition of the surfaces upon which they come into contact, or even of the surrounding environment (such as in the case of airborne contaminants). Thus, there is a need for materials comprising flexible substrates, or personal protective articles derived therefrom, comprising sufficient adhesive properties which can enhance the adhesion force of the user to a variety of surfaces, and which can further provide a means for reducing the degree of contamination disposed upon such surfaces, or of the surrounding environment.

In addition, currently available adhesive materials (e.g., double-sided adhesive tape) could be applied to flexible substrates, or personal protective articles derived therefrom, in an attempt to increase adhesiveness to a variety of surfaces. However, it has been found herein that such currently available adhesive materials tend to leave an undesirable residue on the surfaces upon which they come into contact. Thus, there is a need for materials comprising flexible substrates, or personal protective articles derived therefrom, comprising an adhesive and cohesive coating which imparts substantially no residue upon release from such surfaces. Furthermore, currently available coated flexible substrates, particularly those comprising nonwoven fabrics, and personal protective articles derived therefrom, are typically considered to be disposable. For example, attempts to launder such coated substrates and articles result in loss of integrity and degradation of efficacy, particularly of the coating component, (which typically separates or detaches from the substrate and/or loses its intended coating efficacy (such as gripping/adhesive ability, for example)), forcing the user to undesirably discard the substrate or articles after only a single use. Thus, there is a need for coated materials comprising flexible substrates, or personal protective articles derived therefrom, which can be capable of multi-use (e.g., can maintain integrity and/or efficacy after laundering). There is a further need for such coated materials comprising flexible substrates, or personal protective articles derived therefrom, which can be cleansed by conventional washing techniques and restored to full usefulness without necessitating the current expensive discarding and restocking of replacements thereof.

In addition, coated flexible substrates, or personal protective articles derived therefrom, are often used in environments in which microbes (e.g., germs, viruses, bacteria, etc.) are present. However, currently available coated substrates and articles thereof typically fail to provide sufficient adhesive properties while simultaneously providing antimicrobial properties. Thus, there is a need for coated materials comprising flexible substrates, or personal protective articles derived therefrom, which provide sufficient adhesive properties while simultaneously providing antimicrobial properties.

SUMMARY

In response, the invention of the present disclosure solves one or more of the problems and/or needs discussed above. In some aspects, the inventive viscoelastic materials, and personal protective articles derived therefrom, can comprise a coating which further improves the coefficient of friction over currently available friction enhancing coatings. In further aspects, the inventive viscoelastic materials, and personal protective articles derived therefrom, can possess a preselected degree of effective adhesiveness coupled with highly desirable cohesiveness and releasability attributes. In other aspects, the inventive viscoelastic materials, and personal protective articles derived therefrom, can comprise sufficient adhesive properties which can enhance the adhesion force of a user to a variety of surfaces, and which can further provide a means for reducing the degree of contamination disposed upon surfaces upon which they come into contact, or of the surrounding environment. In still other aspects, the inventive viscoelastic materials, and personal protective articles derived therefrom, can comprise an adhesive and cohesive coating which imparts substantially no residue upon release from surfaces upon which it comes into contact. In yet other aspects, the inventive viscoelastic materials, and personal protective articles derived therefrom, can be capable of multi-use (e.g., can maintain integrity and/or efficacy after laundering). In further aspects, the inventive viscoelastic materials, and personal protective articles derived therefrom, can be cleansed by conventional washing techniques and restored to full usefulness without necessitating the current expensive discarding and restocking of replacements thereof. In other aspects, the inventive viscoelastic materials, and personal protective articles derived therefrom, can provide desired adhesive and cohesive properties, while simultaneously providing, releasability, cleansability and/or antimicrobial properties. One or more of the aforementioned unique benefits can be realized by utilizing a unique adhesive and cohesive thermoset viscoelastic polymer which can impart desirable properties including, but not limited to, unique viscoelasticity, adhesiveness, cohesiveness, releasability, cleansability, antimicrobial (e.g., hygienic, antipathogenic, antibacterial, etc.), minimized residue, and the like.

In some aspects, a viscoelastic material comprises a flexible substrate and an adhesive and cohesive thermoset viscoelastic polymer, wherein the polymer comprises about 4 wt % to about 8 wt % isocyanate prepolymer, about 35 wt % to about 55 wt % polyols having repetitive ether groups comprising straight chain linking diols and cross-linking triols, and about 20 wt % to about 60 wt % plasticizer.

In some aspects, the isocyanate prepolymer is a diisocyanate prepolymer, such as methylene diphenyl diisocyanate. In other aspects, the straight chain linking diols are present in an amount of about 0 wt % to about 20 wt % and the cross-linking triols are present in an amount of about 10 wt % to about 50 wt %. In yet other aspects, the straight chain linking diols and cross-linking triols each have a molecular weight ranging from about 1,000 to about 10,000. In still other aspects, the polyols are present in a straight chain linking diols to cross-linking triols weight ratio of about 0:1 to about 1:1. In yet other aspects, the straight chain linking diols comprise polyether diol and the cross-linking triols comprise polyether triol. In still other aspects, the plasticizer comprises about 20 wt % to about 50 wt % triglyceride plasticizer and about 0 wt % to about 40 wt % ester plasticizer. In yet other aspects, the plasticizer is present in a triglyceride plasticizer to ester plasticizer weight ratio of about 1:0 to about 3:2. In still other aspects, the triglyceride plasticizer comprises an epoxidized triglyceride plasticizer and the ester plasticizer comprises a diester plasticizer. In further aspects of such embodiments, the epoxidized triglyceride plasticizer comprises epoxidized vegetable oil and the diester plasticizer comprises dialkyl ester plasticizer. In still further aspects of such embodiments, the epoxidized vegetable oil comprises epoxidized soybean oil and the dialkyl ester plasticizer comprises dibutyl sebacate.

In some aspects, the adhesive and cohesive thermoset viscoelastic polymer component is at least partially disposed upon a surface of the flexible substrate component of the viscoelastic material in the form of a coating. In other aspects, the polymer coating has a thickness of about 0.1 mm to about 10 mm.

In some aspects, the viscoelastic material further comprising at least one additive selected from initiators, catalysts, UV inhibitors, antioxidants and colorants. In other aspects, the viscoelastic material exhibits viscoelastic, adhesive, cohesive, releasability, cleansability and antimicrobial properties.

In some aspects, the viscoelastic material is in the form of a personal protective article. In other aspects, the personal protective article is selected from footwear covers, surgical gowns, surgical drapes, gloves, hats, facemasks, coveralls, body suits, mats, pads, and aprons. In one preferred embodiment, the personal protective article is in the form of a footwear cover.

In some aspects, the flexible substrate component of the viscoelastic material is selected from nonwoven fabrics, woven fabrics, rubbers, nitrile, foams, leather, flexible plastics, or combinations thereof.

In some aspects, a footwear cover comprises a viscoelastic material, wherein the viscoelastic material comprises an adhesive and cohesive thermoset viscoelastic polymer coated onto a flexible substrate; wherein the flexible substrate comprises a nonwoven fabric; and wherein the adhesive and cohesive thermoset viscoelastic polymer comprises about 4 wt % to about 8 wt % methylene diphenyl diisocyanate prepolymer, about 0 wt % to about 20 wt % polyether diol, about 10 wt % to about 50 wt % polyether triol, about 20 wt % to about 50 wt % epoxidized soybean oil, and about 0 wt % to about 40 wt % dibutyl sebacate. In further aspects, the footwear cover comprises a polyether diol to polyether triol weight ratio of about 0:1 to about 1:1 and an epoxidized soybean oil to dibutyl sebacate weight ratio of about 1:0 to about 3:2. In other aspects, the adhesive and cohesive thermoset viscoelastic polymer coated onto the flexible substrate is configured as a pattern. In still other aspects, the footwear cover exhibits viscoelastic, adhesive, cohesive, releasability, cleansability and antimicrobial properties.

In some aspects, a method for making a viscoelastic material comprises:
A. providing a flexible substrate;
B. providing a thermosetting reaction media comprising:
   i. about 4 wt % to about 8 wt % diisocyanate prepolymer;
   ii. about 35 wt % to about 55 wt % polyols comprising:
      a) about 0 wt % to about 20 wt % polyether diol, and
      b) about 10 wt % to about 50 wt % polyether triol; and
   iii. about 20 wt % to about 60 wt % plasticizer comprising:
      a) about 20 wt % to about 50 wt % epoxidized triglyceride plasticizer; and
      b) about 0 wt % to about 40 wt % dialkyl ester plasticizer;
C. mixing the thermosetting reaction media to form a polymer mix;
D. applying the polymer mix onto the flexible substrate to form a polymer mix coating; and
E. allowing the polymer mix coating to fully cure to form an adhesive and cohesive thermoset viscoelastic polymer.

In other aspects, the method further comprises fabricating the viscoelastic material into a personal protective article. In still other aspects, the diisocyanate prepolymer is methylene diphenyl diisocyanate, the epoxidized triglyceride plasticizer is epoxidized soybean oil, and the dialkyl ester plasticizer is dibutyl sebacate. In yet other aspects, the thermosetting reaction media further comprises a polyether diol to polyether triol weight ratio of about 0:1 to about 1:1 and an epoxidized triglyceride plasticizer to dialkyl ester plasticizer weight ratio of about 1:0 to about 3:2

In some aspects, a method for making an adhesive and cohesive personal protective article comprises:
A. providing an uncoated personal protective article comprising a flexible substrate;
B. providing a thermosetting reaction media comprising:
   i. about 4 wt % to about 8 wt % diisocyanate prepolymer;
   ii. about 35 wt % to about 55 wt % polyols comprising:
      a) about 0 wt % to about 20 wt % polyether diol, and
      b) about 10 wt % to about 50 wt % polyether triol; and
   iii. about 20 wt % to about 60 wt % plasticizer comprising:
      a) about 20 wt % to about 50 wt % epoxidized vegetable oil; and
      b) about 0 wt % to about 40 wt % dialkyl ester plasticizer;
C. mixing the thermosetting reaction media to form a polymer mix;
D. applying the polymer mix onto the flexible substrate of the uncoated personal protective article to form a polymer mix coating; and
E. allowing the polymer mix coating to fully cure to form an adhesive and cohesive thermoset viscoelastic polymer.

In other aspects, the diisocyanate prepolymer is methylene diphenyl diisocyanate, the epoxidized vegetable oil plasticizer is epoxidized soybean oil, and the dialkyl ester plasticizer is dibutyl sebacate. In still other aspects, the thermosetting reaction media further comprises a polyether diol to polyether triol weight ratio of about 0:1 to about 1:1 and an epoxidized vegetable oil plasticizer to dialkyl ester plasticizer weight ratio of about 1:0 to about 3:2.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

Figure 8:
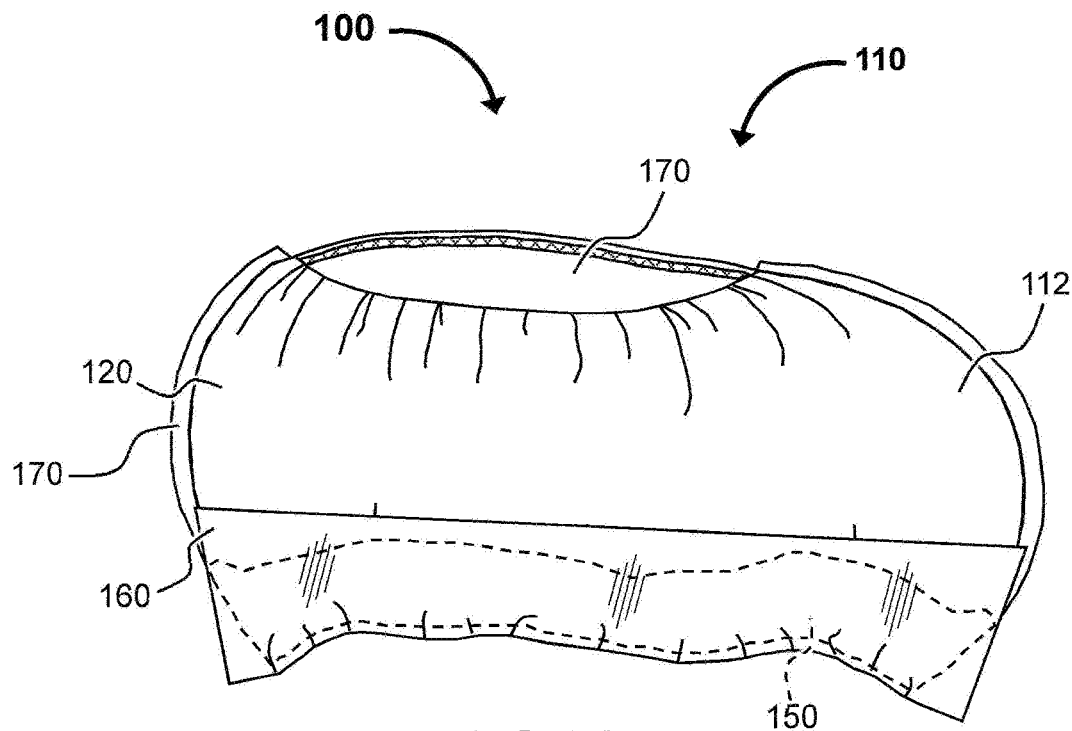
Figure 9A:
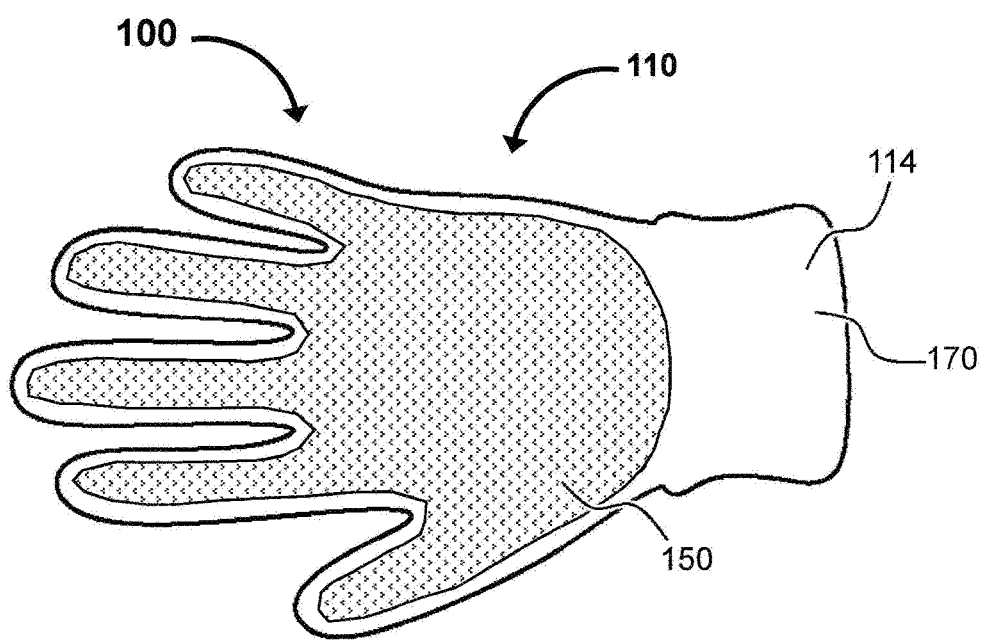
Figure 9B:
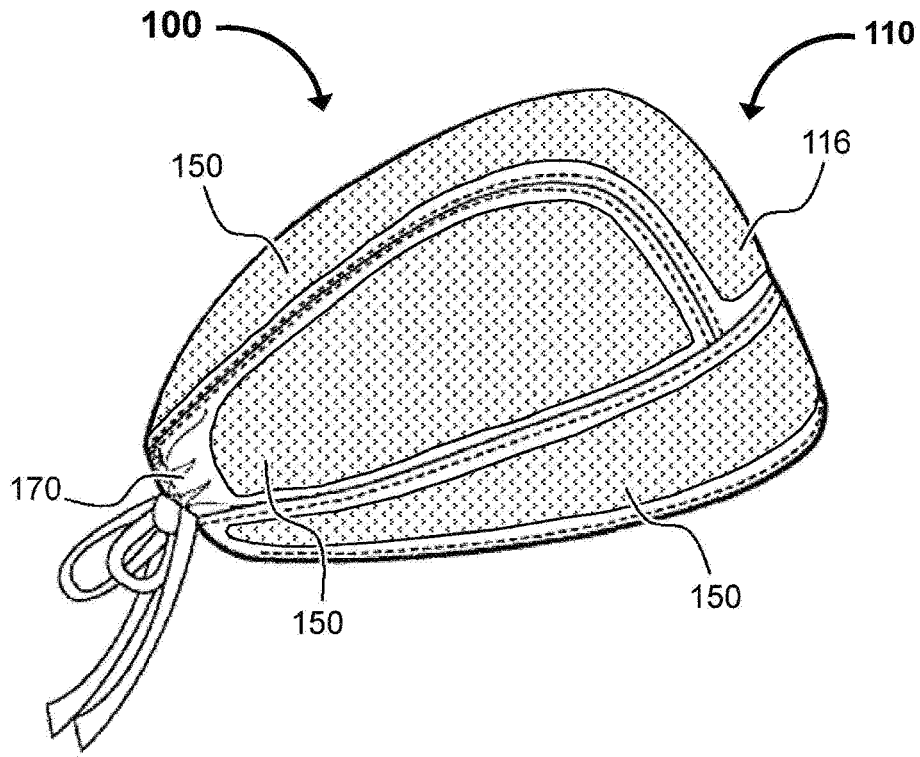
Figure 9C:
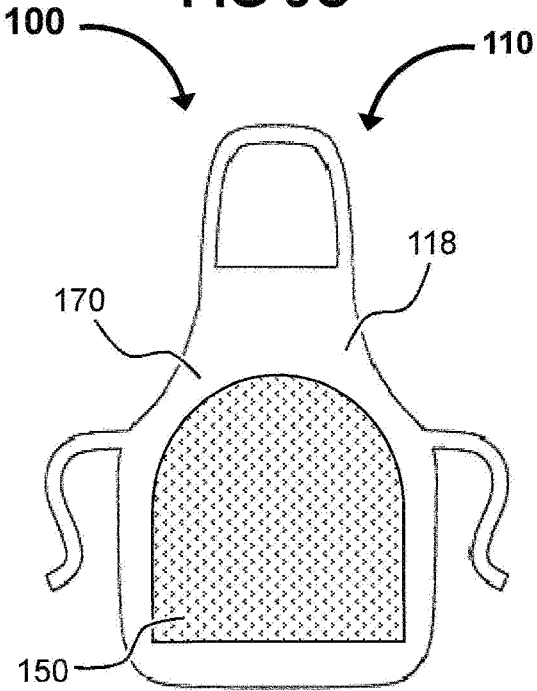

FIG. 8 is a side perspective view showing an inventive personal protective article in the form of a footwear cover in a closed, substantially laid-flat configuration formed from an inventive viscoelastic material comprising a flexible substrate partially coated with an adhesive and cohesive thermoset viscoelastic polymer of the present disclosure, and further comprising a release substrate disposed upon the polymer thereof;

FIG. 9A is a perspective view showing an inventive personal protective article in the form of a glove formed from an inventive viscoelastic material comprising a flexible substrate which is partially coated upon the exterior surface thereof with an adhesive and cohesive thermoset viscoelastic polymer of the present disclosure;

FIG. 9B is a side perspective view showing an inventive personal protective article in the form of a hat formed from an inventive viscoelastic material comprising a flexible substrate and a plurality of adhesive and cohesive thermoset viscoelastic polymer coatings of the present disclosure disposed upon the exterior surface thereof;

FIG. 9C is a perspective view showing an inventive personal protective article in the form of an apron formed from an inventive viscoelastic material comprising a flexible substrate which is partially coated with an adhesive and cohesive thermoset viscoelastic polymer of the present disclosure; and FIG. 10 is a schematic view showing a non-limiting exemplary polymer application process in the form of spraying system.

Repeated use of reference characters in the present specification and drawings is intended to represent the same or analogous features or elements of the present invention.

Test Methods

Adhesiveness, cohesiveness and releasability properties can be measured using the test method described in Appendix A of the aforementioned cross-referenced related applications. Such properties can also be measured using standardized test methods known to persons having skill in the art, such as ASTM D1876 Peel Resistance of Adhesives (T-Peel Test), as well as other standardized Peel Tests such as the ASTM 90-Degree Test and ASTM 180-Degree Test, which are used when a flexible material has been bonded to a rigid substrate such as plastic or metal.

Definitions

It should be noted that, when employed in the present disclosure, the terms "a" and "an" are intended to mean "at least one" of any stated features, elements, integers, steps, components, or groups and are not intended to be limited to only one of such features, elements, integers, steps, components, or groups thereof, except where specifically stated as such. In addition, use of the phrase "at least one" is not intended to render other uses of the terms "a" or "an" to be limited to only one of a feature, element, integer, step, component, or group.

It should be noted that, when employed in the present disclosure, the terms "comprises," "comprising" and other derivatives from the root term "comprise" are intended to be open ended terms that specify the presence of any stated features, elements, integers, steps, components, or groups, and are not intended to preclude the presence or addition of one or more other features, elements, integers, steps, components, or groups thereof.

As used herein, the term "coform" refers to a process in which at least one meltblown die head is arranged near a chute through which other materials are added to the web while it is forming. Such other materials may be pulp, cellulose or staple fibers, for example.

As used herein the term "meltblown fibers" refers to fibers formed by extruding a molten thermoplastic material through a plurality of fine, usually circular, die capillaries as molten threads or filaments into converging high velocity, usually hot, gas (e.g., air) streams that attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Meltblown fibers may be continuous or discontinuous, are generally smaller than 10 microns in average diameter, and are generally tacky when deposited onto the collecting surface.

As used herein with respect to nonwovens, "laminate" and "multilayer laminate" refers to a laminate wherein some of the layers are spunbond or some meltblown such as a spunbond/meltblown/spunbond (SMS) laminate, and others. Such a laminate may be made by sequentially depositing onto a moving forming belt first a spunbond fabric layer, then a meltblown fabric layer and lastly another spunbond layer, and then bonding the laminate. Alternatively, the fabric layers may be made individually, collected in rolls, and combined in a separate bonding step. Such fabrics usually have a basis weight of from about 0.1 osy to about 12 osy (6 gsm to 400 gsm), such as from about 0.75 osy to about 3 osy (25 gsm to 100 gsm). Multilayer laminates may also have various numbers of meltblown layers or multiple spunbond layers in many different configurations and may include other materials like films or coform materials, e.g. SMMS, SM, SFS, etc.

As used herein, the term "nonwoven fabric" refers to a web having a structure of individual fibers or threads that are randomly interlaid, but not in an identifiable manner or pattern as in a woven or knitted fabric.

As used herein, the term "spunbond fibers" or "spunbonded fibers" refers to small diameter fibers that are formed by extruding molten thermoplastic material as filaments from a plurality of fine, usually circular capillaries of a spinneret with the diameter of the extruded filaments then being rapidly reduced. Spunbond fibers are generally not tacky when they are deposited onto a collecting surface. Spunbond fibers are generally continuous and have average diameters larger than about 7 microns, such as between about 10 microns and about 20 microns.

As used herein, the terms "viscoelastomeric" and "viscoelastic" are used interchangeably to refer to a substance having viscous and elastic properties.

These terms may be defined with additional language in the remaining portions of the specification.

DETAILED DESCRIPTION

The invention is generally directed to inventive viscoelastic materials comprising flexible substrates which are at least partially coated with an inventive adhesive and cohesive thermoset viscoelastic polymer, as well as to inventive adhesive and cohesive personal protective articles derived therefrom. Such inventive materials and articles thereof can exhibit unique viscoelastic, adhesive, cohesive, releasability, cleansability, and/or antimicrobial properties.

In some aspects, the inventive viscoelastic materials, and inventive personal protective articles derived therefrom, can comprise a coating which further improves the coefficient of friction over currently available friction enhancing coatings. In further aspects, the inventive viscoelastic materials, and inventive personal protective articles derived therefrom, can possess a preselected degree of effective adhesiveness coupled with highly desirable cohesiveness and releasability attributes. In other aspects, the inventive viscoelastic materials, and inventive personal protective articles derived therefrom, can comprise sufficient adhesive properties which can enhance the adhesion force of a user to a variety of surfaces, and which can further provide a means for reducing the degree of contamination disposed upon surfaces upon which they come into contact, or of the surrounding environment. In still other aspects, the inventive viscoelastic materials, and inventive personal protective articles derived therefrom, can comprise an adhesive and cohesive coating which imparts substantially no residue upon release from surfaces upon which it comes into contact. In yet other aspects, the inventive viscoelastic materials, and inventive personal protective articles derived therefrom, can be capable of multi-use (e.g., can maintain integrity and/or efficacy after laundering). In further aspects, the inventive viscoelastic materials, and inventive personal protective articles derived therefrom, can be cleansed by conventional washing techniques and restored to full usefulness without necessitating the current expensive discarding and restocking of replacements thereof. In other aspects, the inventive viscoelastic materials, and inventive personal protective articles derived therefrom, can provide desired adhesive and cohesive properties, while simultaneously providing, inter alio, antimicrobial properties. One or more of the aforementioned unique benefits can be realized by utilizing a unique adhesive and cohesive thermoset viscoelastic polymer which can impart desirable properties including, but not limited to, unique viscoelasticity, adhesiveness, cohesiveness, releasability, cleansability, antimicrobial (e.g., hygienic, antipathogenic, antibacterial, etc.), minimized residue, and the like.

The inventive viscoelastic materials, and inventive personal protective articles derived therefrom, have an exceptional affinity to provide adhesive grip, to adhesively attract contaminants, and to cohesively release from objects (e.g., flooring, tools, etc.) upon which they come into contact. For example, the unique adhesive and cohesive release attributes provided by the inventive viscoelastic materials herein, and inventive personal protective articles derived therefrom, effectuates a release of objects wherein the surfaces of such objects upon which they come into contact are substantially free from any polymeric residue. In another example, the inventive viscoelastic materials herein, and inventive personal protective articles derived therefrom, can retain their effective antimicrobial capacity throughout their use (at least until the maximum contamination or saturation level has been attained). However, unlike conventional personal protective articles, particularly those comprising nonwoven materials, which must be discarded after use due to degradation and/or contamination, the present inventive viscoelastic materials, and inventive personal protective articles derived therefrom, may be restored to their original adhesive, cohesive and antimicrobial efficacy by conventional cleansing techniques, such as by washing (e.g. via handwashing, conventional washing machine washing, autoclaving, etc.). Also, unlike conventional personal protective articles, the inventive viscoelastic materials, and inventive personal protective articles derived therefrom, also uniquely possess antimicrobial properties which renders them particularly useful for a host of hygienic applications.

The unique inventive viscoelastic materials and inventive personal protective articles thereof of the present invention are provided by incorporating a unique cleansable, releasable, antimicrobial, adhesive and cohesive thermoset viscoelastomeric polymer component onto a surface, preferably an exterior surface, of the flexible substrate component of the materials and articles so as to operationally interface onto a surface of an object. In one aspect of the present invention, a particularly effective adhesive and cohesive thermoset viscoelastomeric polymer component for forming the inventive viscoelastic materials, and inventive personal protective articles derived therefrom, is a thermoset reaction product prepared from a thermosetting reaction media comprised of a substantially uniform admixture of from about 4 percent to about 8 percent by weight (wt %) of an isocyanate prepolymer, from about 35 percent to about 55 percent by weight polyols with said polyols consisting essentially of a straight chain linking diol and a cross-linking triol, each having repetitive ether groups at a diol to triol weight ratio ranging from about 0:1 to about 1:1, and from about 20 percent to about 60 percent by weight of a plasticizer containing less than about 50 percent by weight of an epoxidized triglyceride plasticizer and from about 0 percent to about 40 percent by weight of an ester plasticizer, with the plasticizer being uniformly and cohesively dispersed and bound throughout the reaction product. Typically the useful polyols will be comprised of liquid polyethers having a molecular weight of about 1000 to about 10,000.

Although several exemplary embodiments of the present invention will be described herein, it should be understood that the disclosed embodiments are intended merely as non-limiting examples of the invention that may be embodied in various forms. Therefore, specific details disclosed herein, such as relating to structure, function, and the like, are not to be interpreted as limiting in any manner whatsoever, but rather only as one of numerous example bases for claims and/or teaching persons having ordinary skill in the art to variously employ the present invention in virtually any appropriately detailed structure or circumstance.

Accordingly, in the interest of brevity and conciseness, descriptions herein may be substantially directed to the non-limiting exemplary form of inventive personal protective articles comprising the inventive viscoelastic materials of the present disclosure. More particularly, descriptions herein will be substantially directed to a non-limiting exemplary embodiment in the form of a footwear cover comprising the inventive viscoelastic materials of the present disclosure, wherein the inventive viscoelastic materials comprise a flexible substrate in the form of a nonwoven fabric coated with an inventive adhesive and cohesive thermoset viscoelastic polymer. Such footwear covers are typically worn upon a user's foot, including a bare foot, a foot comprising a stocking, a foot comprising a shoe, a foot comprising a boot, and the like, wherein the user's foot is disposed within the interior of the footwear covers. Footwear covers can be utilized wherever protection of and/or from the foot is desired (e.g., including protection of an object and/or the surroundings from contaminants of the foot, as well as protection of the foot from contaminants from an object and/or of the surroundings), and are particularly useful for new home showings, hospital/surgical rooms, cleanrooms, and laboratories, for example. However, it should be understood that that the present invention is suitable for use with various other articles (e.g., surgical gowns, surgical drapes, gloves, hats, facemasks, coveralls, body suites, mats, pads, aprons, etc.), and various other uses, without departing from the scope of the invention. Several non-limiting exemplary embodiments of other suitable inventive personal protective articles are illustrated in FIGS. 9A-9C.

Figure 1A:
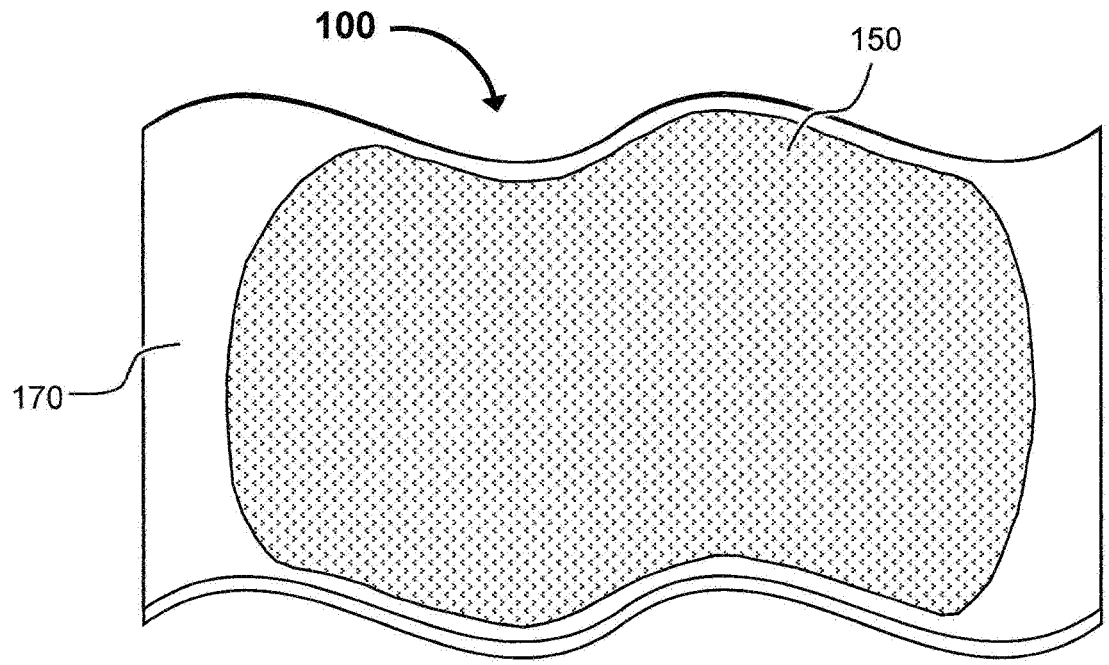
FIG. 1A is a perspective view showing an inventive viscoelastic material comprising a flexible substrate partially coated with an adhesive and cohesive thermoset viscoelastic polymer of the present disclosure.
Figure 1B:
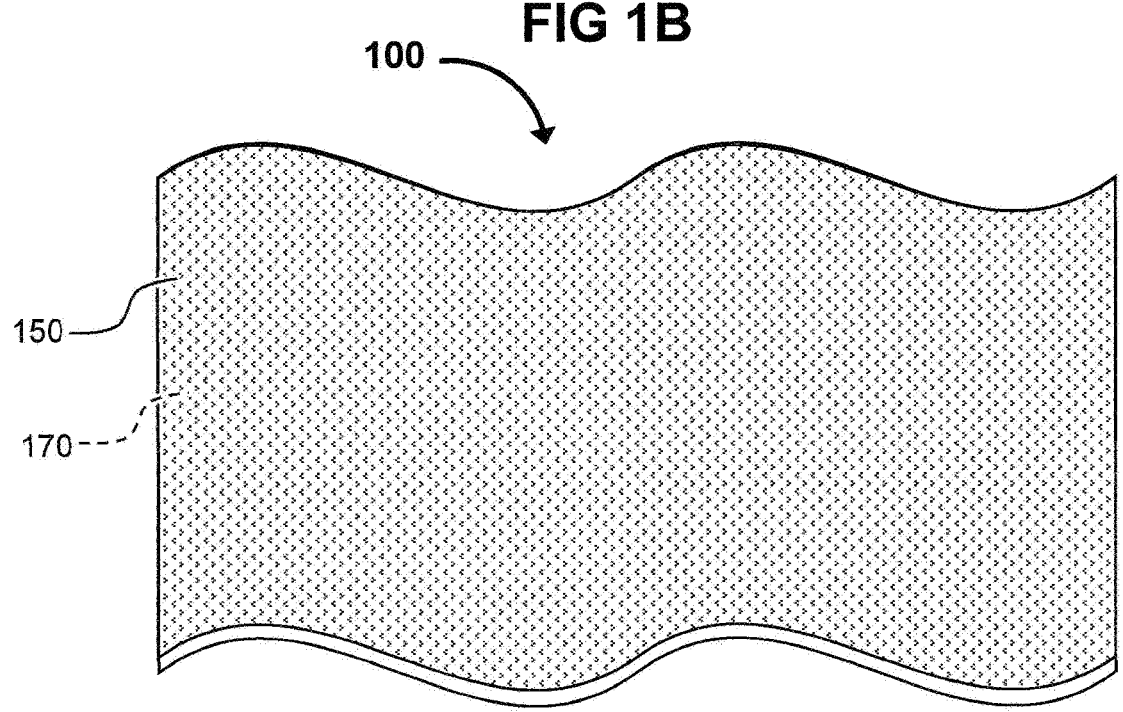
FIG. 1B is a perspective view showing an inventive viscoelastic material comprising a flexible substrate substantially coated with an adhesive and cohesive thermoset viscoelastic polymer of the present disclosure.

To gain a better understanding of the present invention, attention is directed to FIGS. 1A-1B for exemplary purposes showing non-limiting embodiments of an inventive viscoelastic material 100 of the present disclosure. As illustrated, the viscoelastic material 100 is shown in a sheet form, comprising an adhesive and cohesive thermoset viscoelastic polymer 150 of the present invention disposed upon a flexible substrate 170. FIG. 1A illustrates the flexible substrate 170 being partially coated with the polymer 150 to form the inventive viscoelastic material 100, and FIG. 1B illustrates the flexible substrate 170 being substantially entirely coated with the polymer 150 to form the inventive viscoelastic material 100. It should be understood that, due to a number of variables (e.g., the porous or fibrous nature of the flexible substrate 170, the viscosity of the polymer 150 at the time of coating, etc.), the polymer 150 may be disposed substantially atop the exterior surface of the flexible substrate 170, or may be at least partially disposed within the infrastructure of the flexible substrate 170, without departing from the scope of the invention.

Figure 2A:
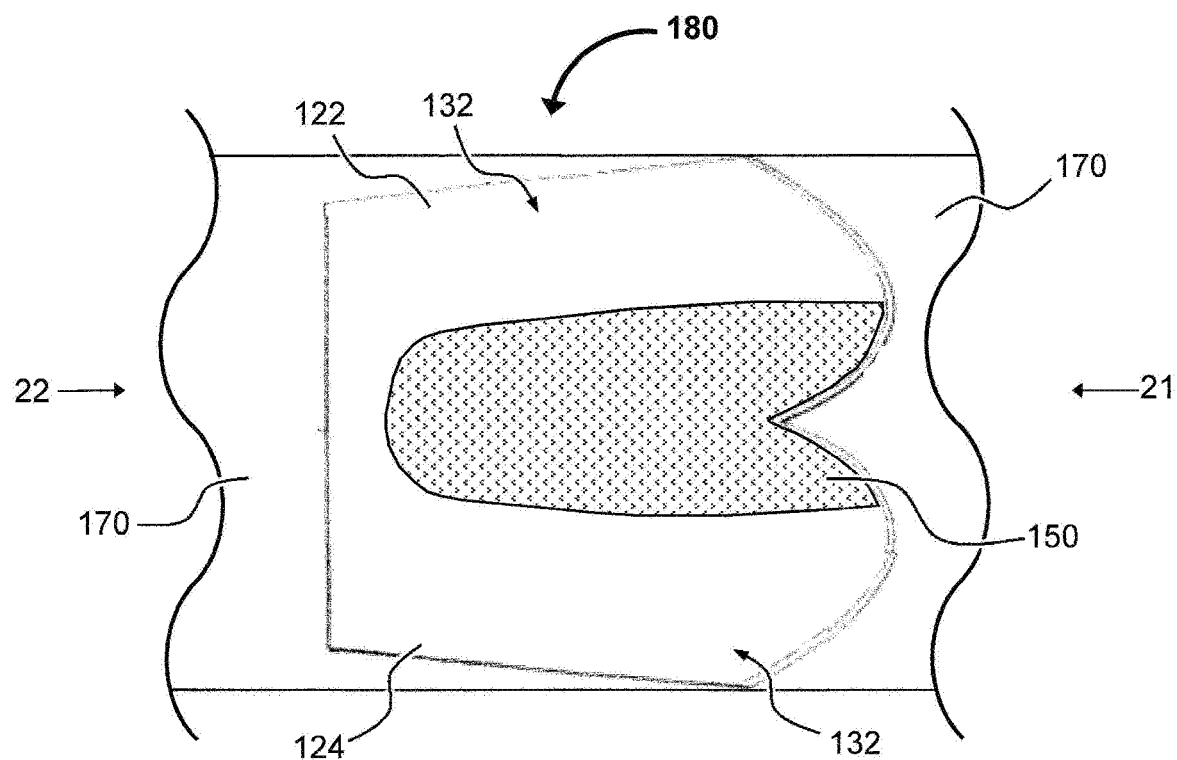
FIG. 2A is a top view of a flexible substrate comprising a blank of a personal protective article in the form of a footwear cover cut therein, wherein the blank is partially coated with an adhesive and cohesive thermoset viscoelastic polymer of the present disclosure to form an inventive viscoelastic material.
Figure 2B:
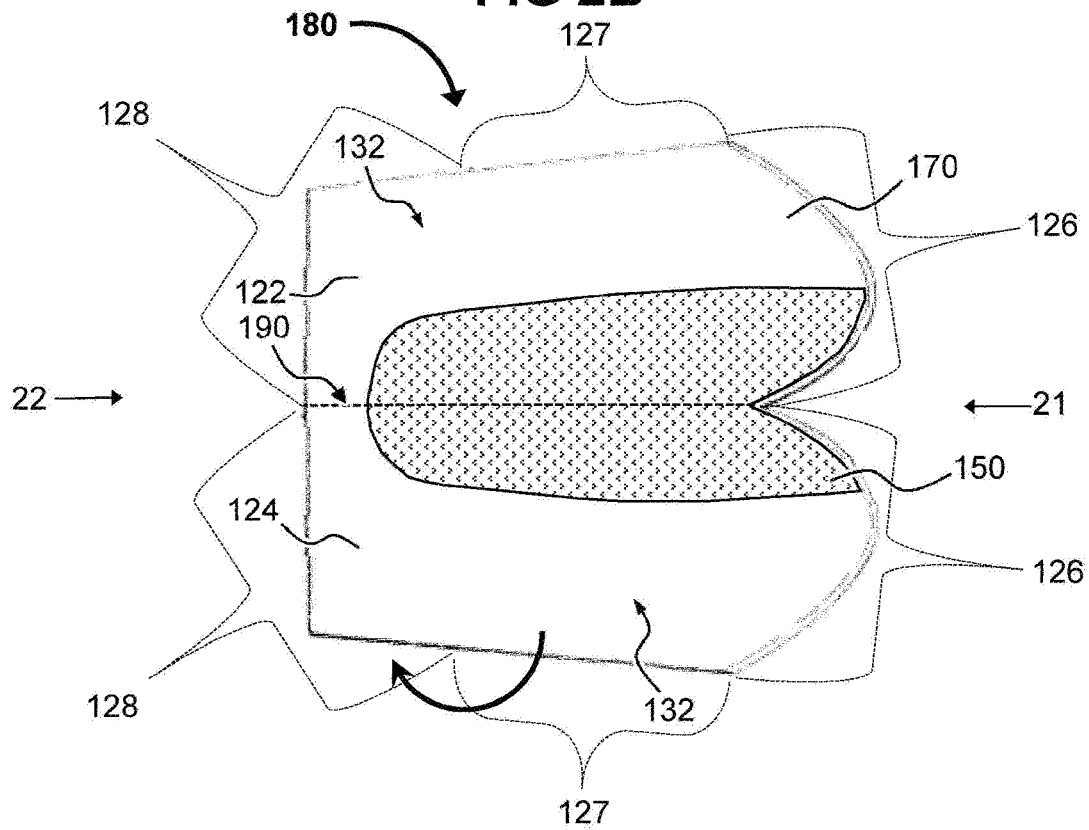
FIG. 2B is a top perspective view of a blank comprising an inventive viscoelastic material comprising a flexible substrate partially coated with an adhesive and cohesive thermoset viscoelastic polymer of the present disclosure prior to formation into an inventive personal protective article in the form of a footwear cover.

Referring now to FIGS. 2A-2B, a blank 180 of a personal protective article 110 can be prepared from a flexible substrate 170 or from the viscoelastic material 100 via suitable means (e.g., cutting, stamping, punching, etc.). In some aspects, the inventive adhesive and cohesive thermoset viscoelastic polymer 150 may be applied to the flexible substrate 170 component prior to preparing the blank 180 (see also FIGS. 1A-1B). In other aspects, the polymer 150 can be applied after preparing the blank 180, thus forming the viscoelastic material 100 from the blank 180 (see e.g., FIG. 2B). In still other aspects, the polymer 150 can be applied simultaneously with preparing the blank 180, thus forming the viscoelastic material 100 and the blank 180 at the same time (see e.g., FIG. 2A). As illustrated in FIG. 2B, the blank 180 can be generally folded in half upon itself along fold edge line 190, whereinafter the front side 21 edge portions 126 can be attached to each other, and the rear side 22 edge portions 128 can be attached to each other, having unattached portions 127 disposed therebetween, to form a non-limiting exemplary adhesive and cohesive personal protective article 110 of the present disclosure in the form of a footwear cover 112 (see e.g., FIG. 3).

Figure 3:
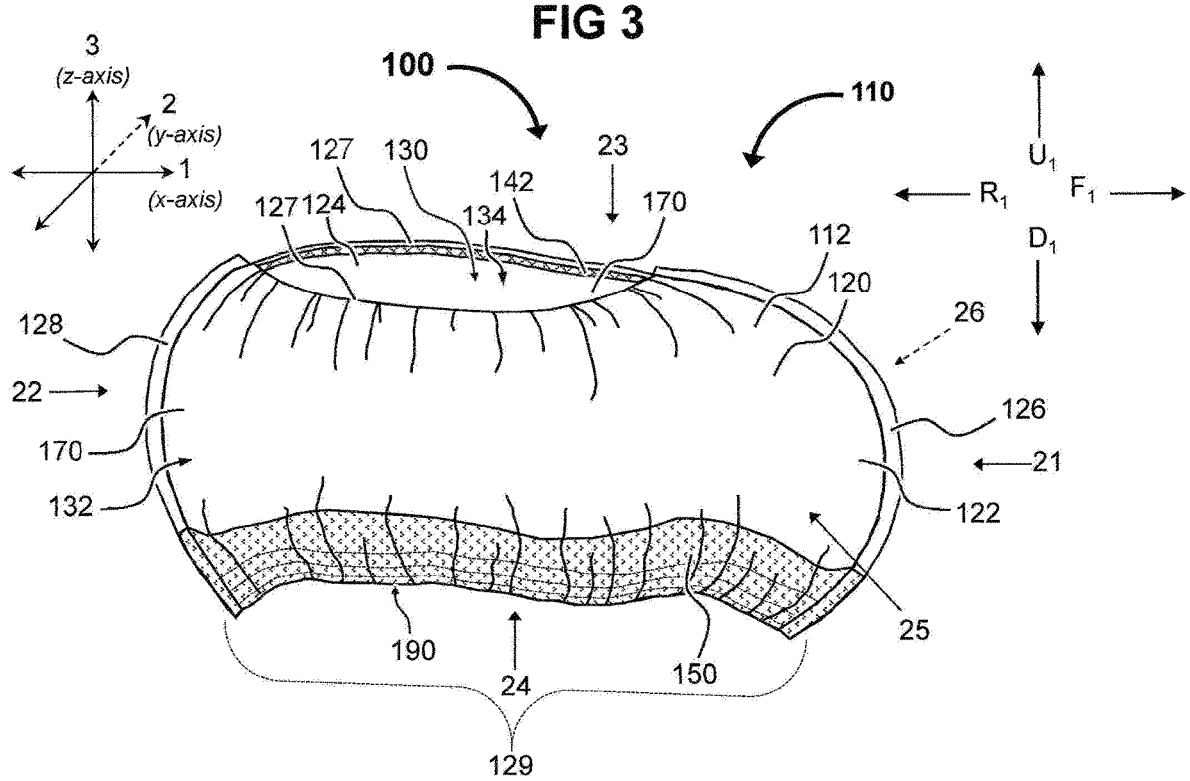
FIG. 3 is a side perspective view showing an inventive personal protective article in the form of a footwear cover in a closed, substantially laid-flat configuration formed from an inventive viscoelastic material comprising a flexible substrate which is partially coated upon the exterior surface thereof with an adhesive and cohesive thermoset viscoelastic polymer of the present disclosure.

Referring now to FIGS. 3-6, several non-limiting exemplary embodiments of inventive adhesive and cohesive personal protective articles 110 of the present disclosure in the form of footwear covers 112 comprising the inventive viscoelastic material 100 herein are shown for exemplary purposes. FIG. 3 illustrates an inventive footwear cover 112 in a closed, laid-flat configuration, such as prior to its first use. FIGS. 4A-6 illustrate an inventive footwear cover 112 in an opened configuration, such as in preparation for donning the footwear cover and/or after the footwear cover has been worn or laundered.

The illustrated footwear cover 112 comprises the inventive viscoelastic material 100 of the present disclosure, and has a front side 21, a rear side 22, a top side 23, a bottom side 24, a first side 25 and a second side 26. The footwear cover 112 comprises a main body 120, which can comprise a flexible substrate 170 base material (e.g., nonwoven fabric, rubber, woven fabric, etc.). The main body 120 can be formed by a pair of panels 122 and 124 (see also FIG. 2B). The panels 122,124 can be can be folded upon a common fold edge 190 which forms a bottom portion 129 of the footwear covers 112, and the front side 21 edges can be attached, and separately the rear side 22 edges can be attached, via suitable attachment means (e.g., stitching, ultrasonic, adhesive, etc.) to form an attached front portion 126 and an attached rear portion 128, having a top side 23 unattached portion 127 disposed therebetween. Accordingly, the top side 23 unattached portion 127 defines an opening 130 for receiving footwear (e.g., a foot, a stocking, a shoe, a boot, and the like) (not shown). In addition, each panel 122,124 includes an exterior surface 132 and an interior surface 134.

Figure 4A:
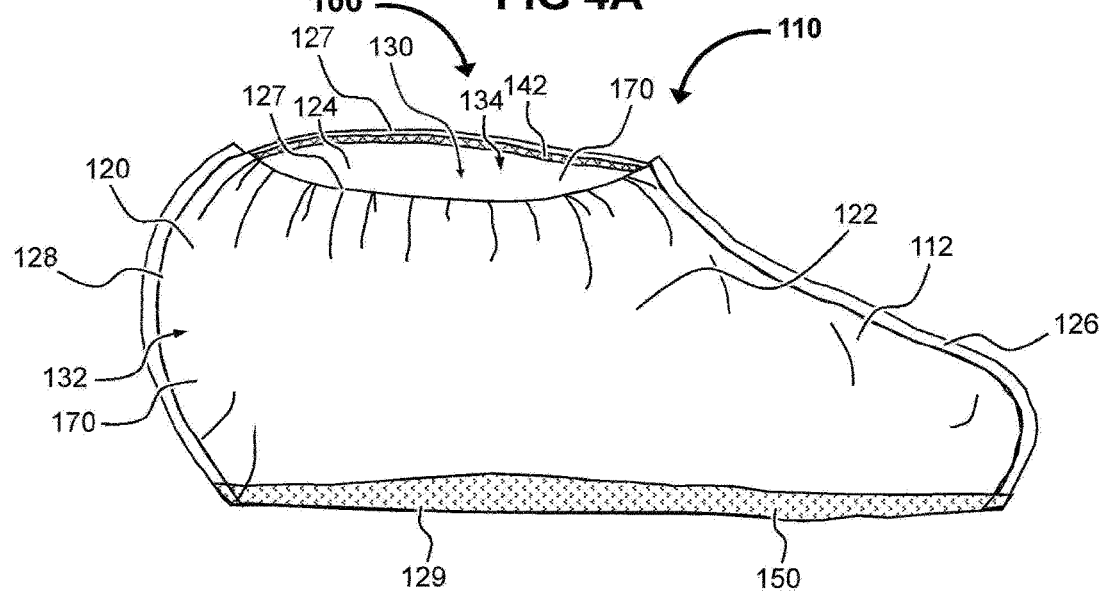
FIG. 4A is a side perspective view showing an inventive personal protective article in the form of a footwear cover in an opened configuration formed from an inventive viscoelastic material comprising a flexible substrate which is partially coated on the exterior surface of its bottom side with an adhesive and cohesive thermoset viscoelastic polymer of the present disclosure.
Figure 4B:
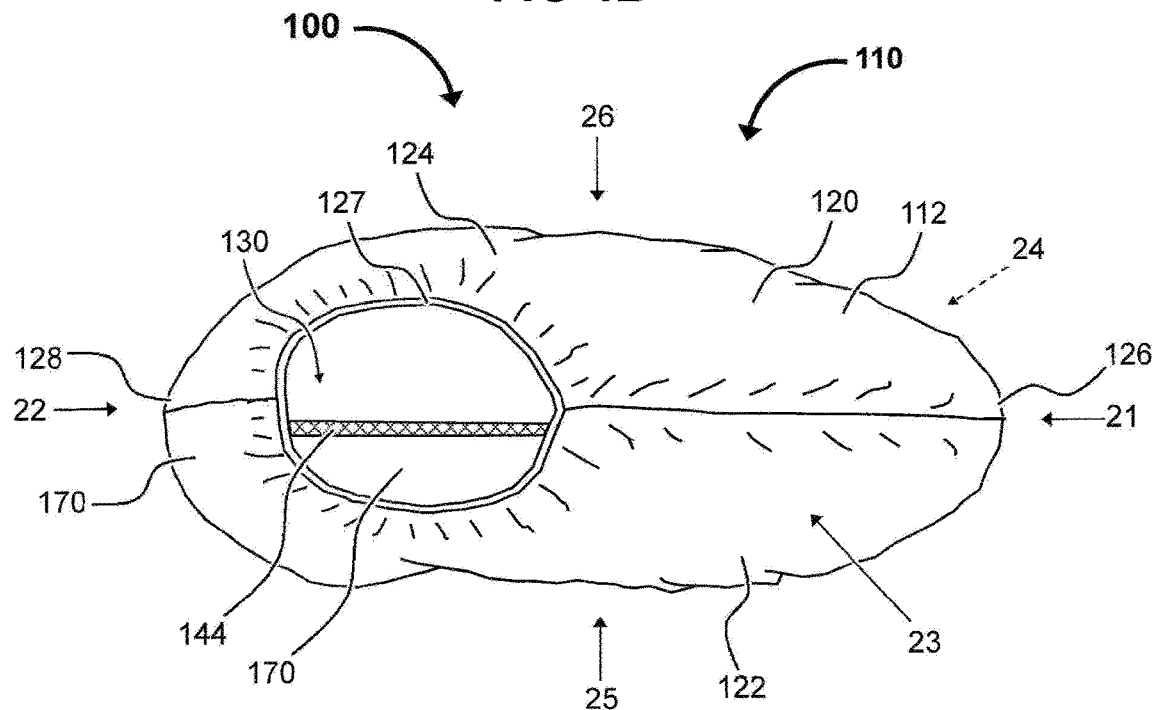
FIG. 4B is a top perspective view of the footwear cover of FIG. 4A.
Figure 4C:
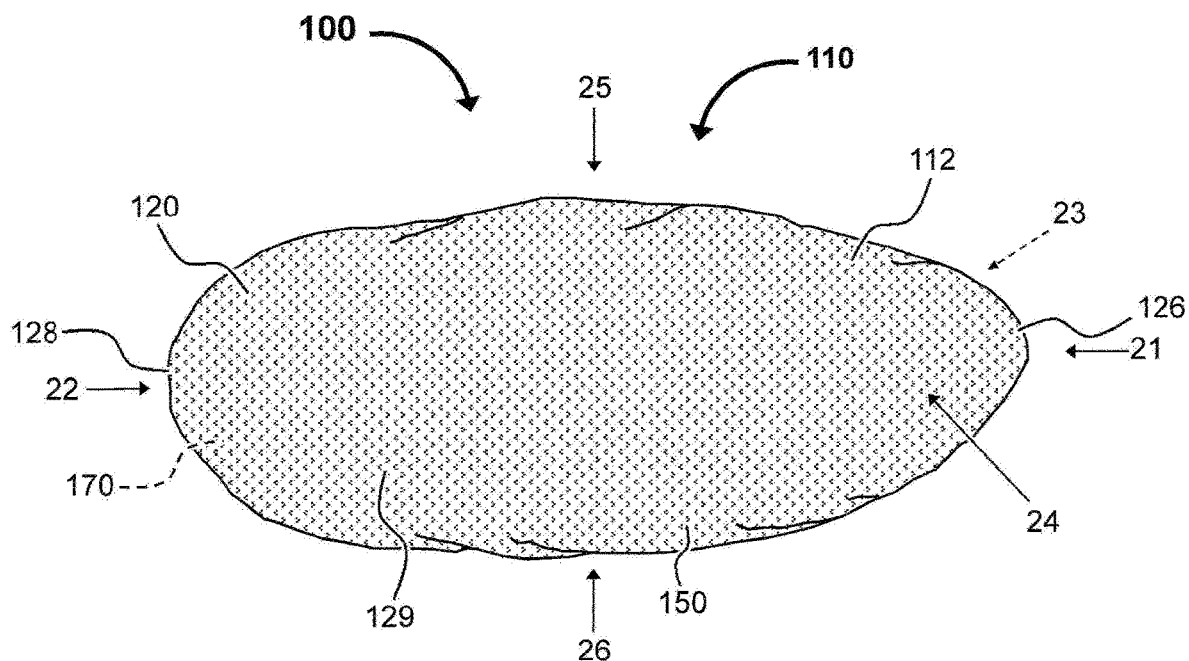
FIG. 4C is a bottom perspective view of the footwear cover of FIG. 4A.
Figure 4D:
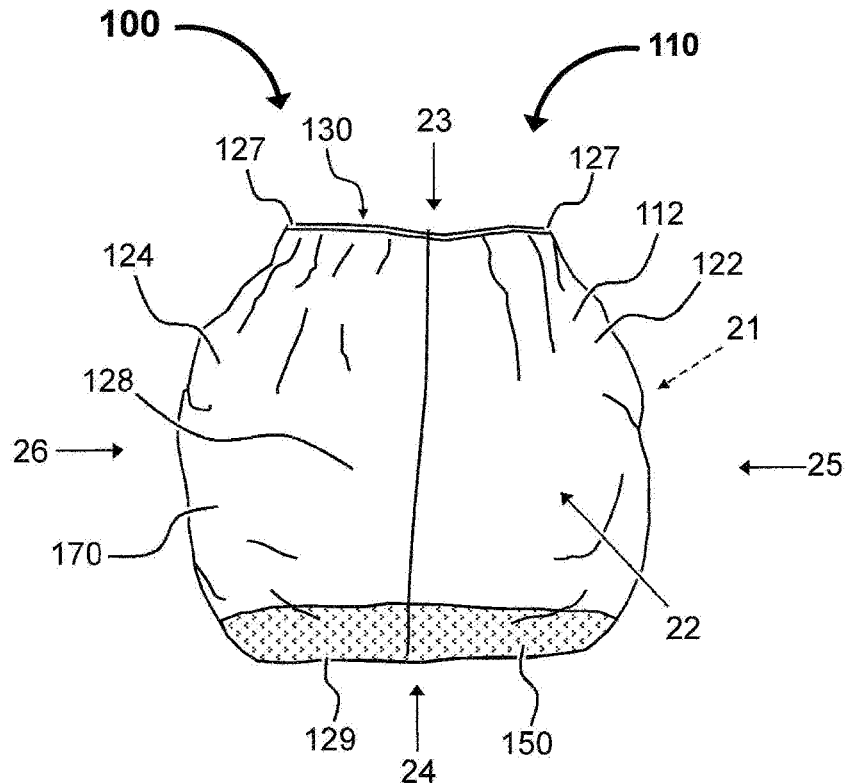
FIG. 4D is a rear perspective view of the footwear cover of FIG. 4A.
Figure 4E:
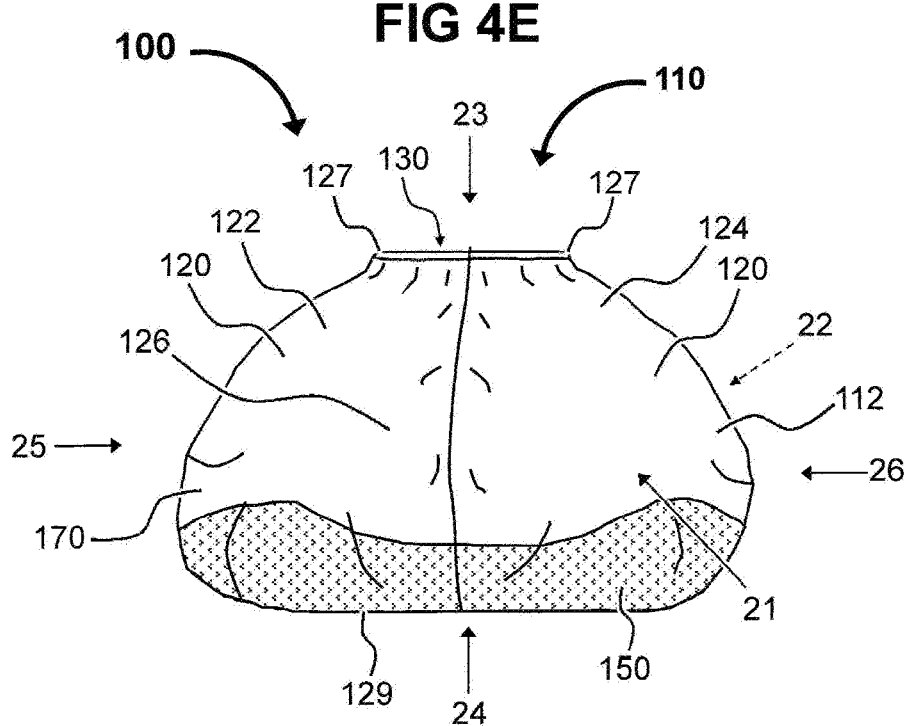
FIG. 4E is a front perspective view of the footwear cover of FIG. 4A.
Figure 5:
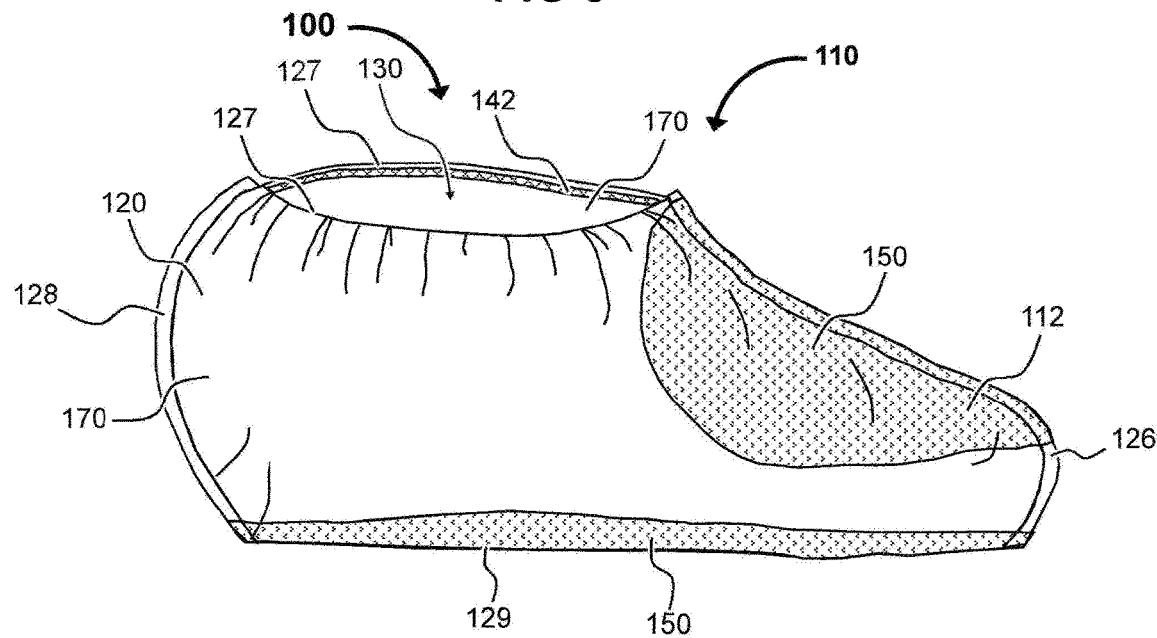
FIG. 5 is a side perspective view showing an inventive personal protective article in the form of a footwear cover in an opened configuration formed from an inventive viscoelastic material comprising a plurality of adhesive and cohesive thermoset viscoelastic polymer coatings of the present disclosure disposed upon the exterior surface thereof.
Figure 6:
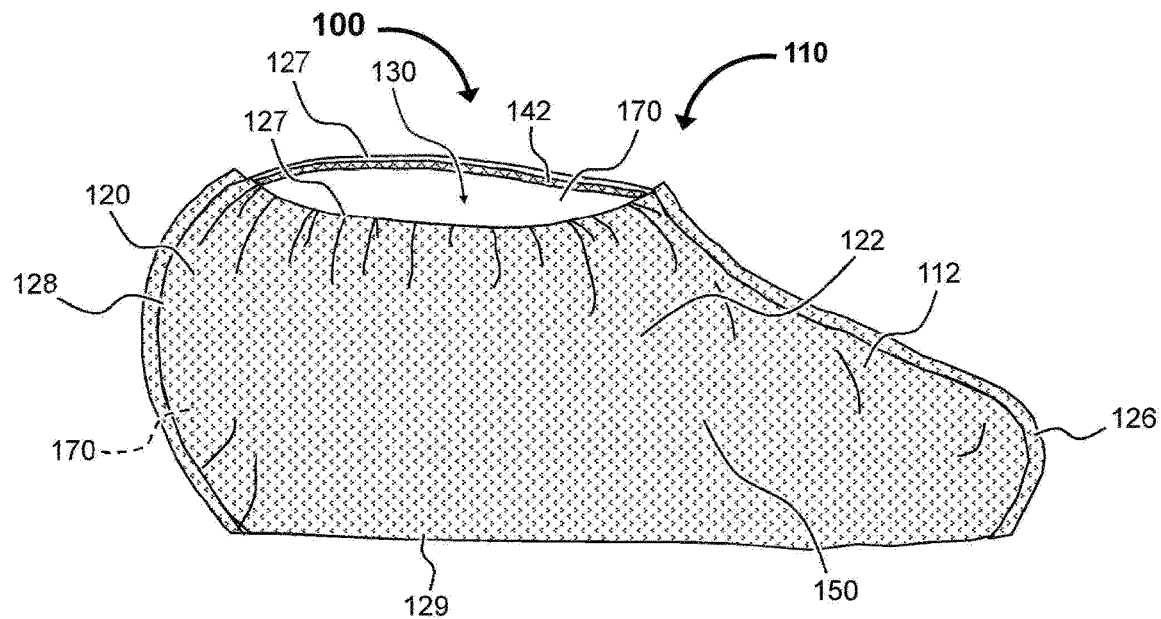
FIG. 6 is a side perspective view showing an inventive personal protective article in the form of a footwear cover in an opened configuration formed from an inventive viscoelastic material comprising an adhesive and cohesive thermoset viscoelastic polymer coating of the present disclosure disposed substantially entirely upon the exterior surface thereof.
Figure 7A:
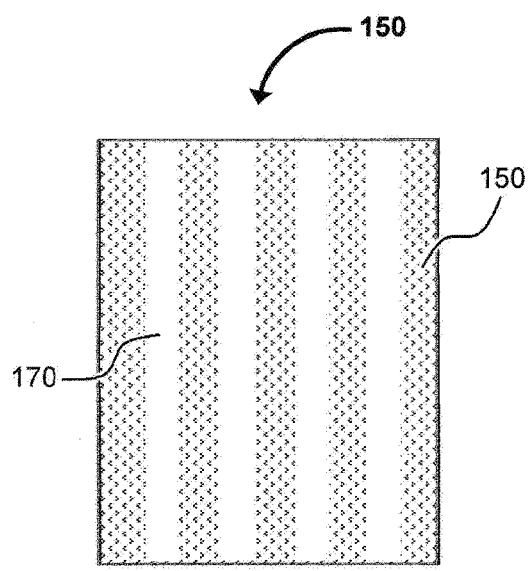
FIG. 7A is a partial view showing a non-limiting exemplary pattern of an adhesive and cohesive thermoset viscoelastic polymer coating of the present disclosure.
Figure 7B:
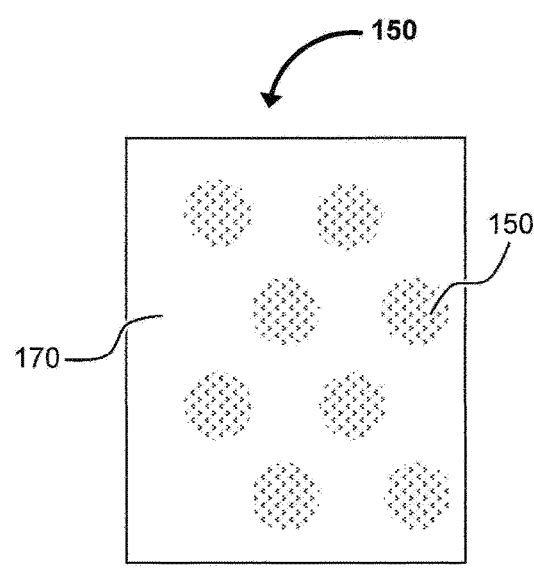
FIG. 7B is a partial view showing a non-limiting exemplary pattern of an adhesive and cohesive thermoset viscoelastic polymer coating of the present disclosure.
Figure 7C:
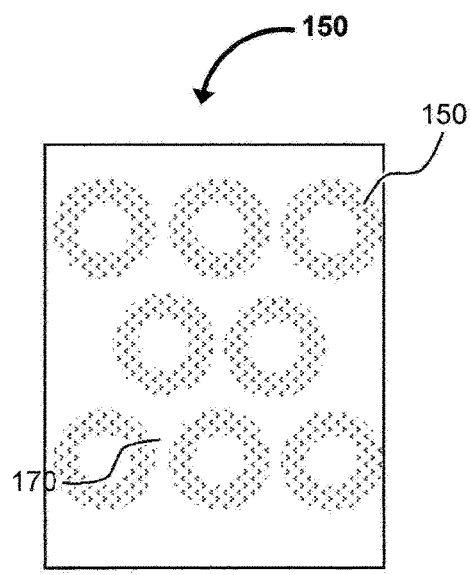
FIG. 7C is a partial view showing a non-limiting exemplary pattern of an adhesive and cohesive thermoset viscoelastic polymer coating of the present disclosure.
Figure 7D:
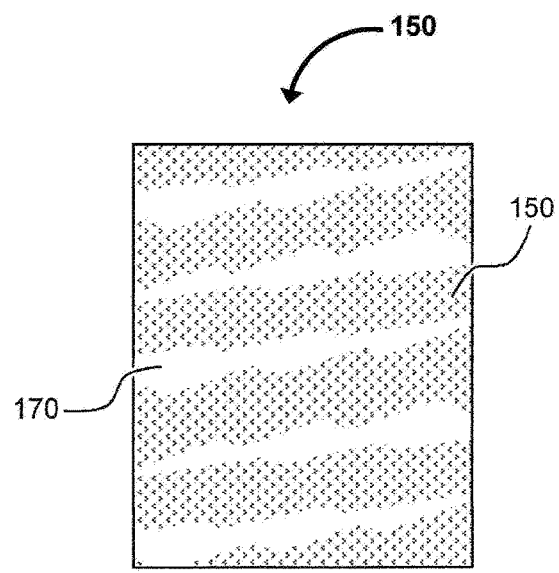
FIG. 7D is a partial view showing a non-limiting exemplary pattern of an adhesive and cohesive thermoset viscoelastic polymer coating of the present disclosure.

The top side 23 unattached portion 127 can optionally include a strip of elastic material 142 which can help keep the footwear covers 112 positioned upon a user during use (see e.g., FIGS. 3 and 4A). Accordingly, the opening 130 can be expandable to be form-fitting about the wearer's body (e.g., the ankles) (not shown). The bottom portion 129 of the footwear covers 112 can also be made expandable by being secured to another optional strip of elastic material 144 (see e.g., FIG. 4B). As a result, the footwear covers 112 can fit more snugly about the toe and heel portions of the sole (not shown), though it need not be.

Although footwear covers 112 can be constructed of a variety of flexible substrates 170, such footwear covers 112 are most typically constructed from flexible substrates 170 in the form of nonwoven fabrics. Thus, for purposes of brevity and conciseness, the following description will primarily describe footwear covers 112 wherein the flexible substrate 170 component of the inventive viscoelastic material 100 and inventive personal protective articles 110 thereof comprise such nonwoven fabrics. However, it should be understood that a variety of other flexible substrate components as would be apparent to persons having ordinary skill in the art can also be utilized with the inventive viscoelastic materials 100 herein and inventive personal protective articles 110 thereof without departing from the scope of the invention.

In addition to the footwear cover 112 embodiments described above, various other methods and configurations can be utilized to form suitable footwear covers 112 without departing from the scope of the invention. For example, other methods and/or configurations are described in U.S. Pat. No. 2,627,126 to O. G. France, U.S. Pat. No. 3,648,109 to Tims et al., U.S. Pat. No. 3,798,503 to Larsh et al., U.S.

Pat. No. 4,019,265 to Epstein, U.S. Pat. No. 4,598,485 to Joe et al., U.S. Pat. No. 4,847,934 to Weber, U.S. Pat. No. 5,822,884 to Roeder, U.S. Pat. No. 6,833,171 to Campbell et al., and U.S. Patent Application No. 2016/0015116 to Jones, which are all herein incorporated by reference in a manner that is consistent herewith As referenced above, in some typical aspects, the footwear cover 112 comprises a flexible substrate 170 component in the form of a nonwoven fabric. Such nonwoven fabrics are typically polymeric fabrics that may be formed from a single layer or multiple layers. In the case of multiple layers, the layers are generally positioned in a juxtaposed or surface-to-surface relationship and all or a portion of the layers may be bound to adjacent layers.

Polymeric nonwoven fabrics are particularly suitable for use in the construction of footwear covers that are designed to be worn in hospitals, cleanrooms, laboratories, kitchens, and other similar environments. Such footwear covers are typically only suitable to be used a single time, and thus are considered to be disposable. The nonwoven fabric component of such footwear covers, in particular fibrous polymeric nonwoven fabrics, may be made according to a variety of processes including, but not limited to, air laid processes, wet laid processes, hydroentangling processes, spunbonding, meltblowing, staple fiber carding and bonding, and solution spinning. The fibers themselves may be made from a variety of dielectric materials including, but not limited to, polyesters, polyolefins, nylons and copolymers of these materials. The fibers may be relatively short, staple length fibers, typically less than 3 inches (7.6 cm) or longer more continuous fibers such as are typically produced by a spunbonding process.

Commercially available nonwoven polymeric fabrics that may be used to construct footwear covers include polypropylene nonwoven fabrics produced by Kimberly-Clark Worldwide, Inc., having a place of business located in Neenah, Wis., U.S.A. For instance, the nonwoven fabric may be a laminate including at least one ply formed from spunbond fibers and another ply formed from meltblown fibers, such as a spunbond/meltblown (SM) nonwoven laminate. In another example, the nonwoven laminate may include at least one ply formed from meltblown fibers that is positioned between two plies formed from spunbond fibers, such as a spunbond/meltblown/spunbond (SMS) nonwoven laminate. Such SMS nonwoven laminates usually have a basis weight of from about 0.1 ounces per square yard (osy) to about 12 osy (3 grams per square meter (gsm) to 400 gsm), or more typically from about 0.75 osy to about 3 osy (25 gsm to 100 gsm). Examples of such nonwoven laminates are disclosed in U.S. Pat. No. 4,041,203 to Brock et al., U.S. Pat. No. 5,169,706 to Collier I V et al., and U.S. Pat. No. 4,374,888 to Bornslaeqer, which are all incorporated herein by reference in a manner that is consistent herewith.

Spunbond fibers may be formed from a polyolefin, for example, polypropylene. One suitable polypropylene is commercially available as PD9355 from Exxon Chemical Company, having a place of business located in Baytown, Tex., U.S.A. Meltblown fibers may be formed from a polyolefin, such as polypropylene and polybutylene or a blend thereof. Examples of such meltblown fibers are contained in U.S. Pat. No. 5,165,979 to Watkins et al. and U.S. Pat. No. 5,204,174 to Daponte et al., both of which are incorporated herein by reference in a manner that is consistent herewith. In some desirable aspects, the meltblown fibers may be formed from a blend of polypropylene and polybutylene. In further aspects, the polybutylene can be present in the blend in a range of from about 0.5 percent to about 20 percent by weight. Examples of such suitable polypropylene are designated as 3746-G from Exxon Chemical Company and as DP-8911 from Shell Chemical Company, having a place of business located in Houston, Tex., U.S.A. The meltblown fibers may also contain a polypropylene modified according to U.S. Pat. No. 5,213,881 to Timmons et al., which is incorporated herein by reference in a manner that is consistent herewith.

Accordingly, in some aspects, the main body 120 of the footwear cover 112 of the present invention can comprise a single nonwoven fabric, a combination of different nonwoven fabrics 170, or a combination of a nonwoven fabric(s) with other flexible substrates, without departing from the scope of the invention.

Continuing now with FIGS. 3-6, in addition to the flexible substrate 170 component, the viscoelastic materials 100 of the present disclosure and inventive personal protective articles 110 thereof, such as in the form of footwear covers 112 for example, also comprises an inventive adhesive and cohesive thermoset viscoelastic polymer 150 (which can exhibit viscoelastic, adhesive, cohesive, releasability, cleansability, and/or antimicrobial properties, as desired). As illustrated, the polymer 150 can desirably be disposed upon at least a portion of at least the exterior surface 132 of the flexible substrate 170 of the main body 120. For example, polymer 150 disposed upon the bottom side 24 of the footwear cover 112 can be useful for providing frictional and adhesive traction to a user, while also serving to adhere contaminants which may be present on a surface upon which the polymer 150 comes into contact (e.g., flooring, a step stool, etc.), thus simultaneously improving the cleanliness of the surfaces upon which it comes into contact (see e.g., FIGS. 4A-4E). In some such aspects, the polymer 150 can additionally neutralize pathogens (e.g., viruses, bacteria, germs, etc.) which may be present upon the surfaces. In other aspects, polymer 150 disposed upon the top side 23, front side 21, rear side 22, first side 25 and/or second side 26 of the footwear covers 112 can be useful for adhering contaminants which may be airborne, or which may fall onto the user's footwear cover 112, thus maintaining or improving the cleanliness of the surrounding environment (see e.g., FIG. 5). In still other aspects, the polymer 150 can be disposed upon substantially the entire exterior surface 132 of the footwear cover 112 for improved benefits (see e.g., FIG. 5). In still other aspects, the polymer 150 component is uniquely cohesive such that the footwear cover 112 can leave substantially no residue upon its release from a surface upon which it comes into contact. In yet other aspects, the footwear cover 112, and polymer 150 component thereof, are cleansable (e.g., via conventional washing techniques) such that the footwear cover 112 can be reusable, even when equivalent conventional footwear covers are considered to be disposable (such as those conventional footwear covers constructed of nonwoven fabrics).

Although the invention can broadly apply to any polymeric adhesive possessing the unique viscoelastic, adhesive, cohesive, releasability, cleansability, and antimicrobial attributes referenced herein, the inventive adhesive and cohesive thermoset viscoelastic polymer 150 herein is particularly well suited for use with personal protective articles 110 of the present disclosure, such as the footwear covers 112 described herein. Such a unique polymer 150 may be derived from a thermosetting reaction media comprised of a substantially uniform admixture of an isocyanate prepolymer, prescribed amounts of polyols in the form of polyether diols and polyether triols, and a carefully balanced ratio of select plasticizers. The isocyanate prepolymer in combination with a balanced ratio and amounts of straight chain diols and cross-linking triols provides a thermoset infrastructure for effectively housing the plasticizing components in a form which unexpectedly contributes to the unique viscoelastic, adhesive, cohesive, releasability and antimicrobial attributes, while also permitting a restorative cleansability function by conventional washing and/or autoclaving techniques. In addition, the unexpected cohesive attributes of the inventive polymer 150 results in no leakage of the plasticizer component, which solves a long standing problem of existing adhesive polymers having plasticizer loadings equivalent to that of the present polymer 150.

A highly effective reaction media for preparing the inventive adhesive and cohesive thermoset viscoelastic polymer 150 of the present disclosure involves providing a thermosetting reaction media comprising: a precursor polymer (also referred to herein as a "prepolymer"), polyols and plasticizer. More particularly, the polymer 150 comprises (i) a prepolymer, such as an isocyanate prepolymer (e.g., a polyol reacted with an isocyanate), preferably a diisocyanate prepolymer (e.g., methylene diphenyl diisocyanate (MDI)), ranging from about 4 percent to about 8 percent by weight of the polymer; (ii) polyols, ranging from about 35 percent to about 55 percent by weight of the polymer, wherein the polyols include straight chain linking polyols (e.g., diols) and cross-linking polyols (e.g., triols); and (iii) plasticizer, ranging from about 20 percent to about 60 percent by weight of the polymer, wherein the plasticizer includes an epoxidized triglyceride plasticizer present in an amount of less than about 50 percent by weight of the polymer. The inventive polymer 150 can also optionally comprise additional components including, but not limited to, additional plasticizers, catalysts, colorants, UV inhibitors, antioxidants, initiators, and the like, as would be apparent to persons having ordinary skill in the art, without departing from the scope of the invention.

As referenced above, the inventive polymer 150 comprises a quantity of prepolymer, such as an isocyanate prepolymer (e.g., a polyol reacted with an isocyanate), preferably a diisocyanate prepolymer (e.g., methylene diphenyl diisocyanate (MDI)), typically ranging from about 4 percent to about 8 percent by weight of the polymer, such as about 5 percent to about 7 percent by weight. In one example, a methylene diphenyl diisocyanate (MDI) designated as ELASTOCAST TQZ-P23, available from BASF Corporation, having a place of business located in Ludwigshafen, Germany, can provide a suitable prepolymer to form the inventive adhesive and cohesive thermoset viscoelastic polymer 150 for use with the inventive viscoelastic materials 100 of the present disclosure, and the inventive adhesive and cohesive personal protective articles 110 thereof.

In addition, the content and the type of polyol reactants in conjunction with the effective use of select plasticizers have been found to have a pronounced effect upon imparting the necessary thermoset polymeric infrastructure for preparing the desired viscoelastic, adhesive, cohesive, releasability, cleansability, and antimicrobial attributes for use as the inventive polymer 150 component for the viscoelastic materials 100 and inventive articles 110 of the present disclosure. Accordingly, an appropriate balance between straight chain producing polyols and cross-linking polyols provides a reaction media suitable for preparing a polyurethane reaction product component (i.e., polymer 150) possessing unexpected useful properties for use with the invention herein.

As referenced above, the inventive polymer 150 also comprises a quantity of polyols, typically ranging from about 35 percent to about 55 percent by weight of the polymer, such as about 40 percent to about 50 percent by weight. More particularly, the polyols include straight chain linking polyols and cross-linking polyols. In some desirable aspects, the straight chain linking polyols are in the form of diols, and the cross-linking polyols are in the form of triols. The diols and triols components of the polymer 150 are typically liquid at room temperature (i.e., about 21° C.) and generally have a molecular weight of about 1,000 to about 20,000, such as about 1,000 to about 15,000, or about 1,000 to about 10,000. The adhesiveness and cohesiveness of the polymer 150 depend upon using a proper polyol balance within the thermosetting reaction media. It has been discovered herein that the weight ratio of diols to triols (in the presence of an effective amount of plasticizer within the reaction media) can suitably fall within a prescribed diol to triol weight ratio range of about 0:1 to about 1:1 to provide the desired viscoelastic, adhesive, cohesive, releasability, cleansability, and/or antimicrobial attributes for effective use herein. The content and type of linking polyols can have a pronounced effect upon imparting the necessary thermoset polymeric infrastructure for obtaining the inventive polymer 150 attributes herein. Thus, an appropriate balance within the cited range between the straight chain producing diols and cross-linking triols can provide an effective reaction media for preparing a thermoset viscoelastomeric polyurethane reaction product uniquely possessing the adhesive, cohesive, releasability, cleansability, and antimicrobial compositional properties for the inventive viscoelastic materials 100 and inventive personal protective articles 110 of the present disclosure.

In general, the diol component of the polymer 150 can provide sufficient cross-linkage disruption and straight chain infrastructure formation to permit for a highly effective intermolecular plasticizer attraction and alignment, thus providing for a highly effective loading of the viscoelastomeric thermoset with the adhesive, cohesive and antimicrobial contributing plasticizer co-factors. In some desirable aspects, the straight chain diol can be provided by a polyether diol having a molecular weight suitably ranging from about 2,000 to about 6,000. Such polyether diol can be suitably present in an amount ranging from 0 to about 20 percent by weight of the polymer, such as about 5 percent to about 15 percent by weight. In one example, a 2 functional polyether diol, designated as ELASTOCAST C4057, available from BASF Corporation, can provide a suitable diol component to form the inventive polymer 150 for use with the inventive viscoelastic materials 100 and inventive personal protective articles 110 of the present disclosure.

In general, the triol component of the polymer 150 can provide sufficient cross-linkage infrastructure to the polymer 150, and can contribute to the unexpected cohesiveness and releasability attributes of the inventive polymer 150. In some desirable aspects, the cross-linking triol can be provided by a polyether triol having a molecular weight suitably ranging from about 3,000 to about 7,000. Such polyether triol can be suitably present in an amount ranging from about 10 percent to about 50 percent by weight of the polymer, such as about 20 percent to about 40 percent by weight. In one example, a 3 functional polyether triol, designated as ELASTOCAST C4018, available from BASF Corporation, can provide a suitable triol component to form the inventive polymer 150 for use with the inventive viscoelastic materials 100 and inventive personal protective articles 110 of the present disclosure.

As referenced above, the inventive polymer 150 also comprises a quantity of plasticizer typically ranging from about 20 percent to about 60 percent by weight of the polymer, such as about 30 percent to about 50 percent by weight. More particularly, the plasticizer includes a triglyceride plasticizer, and can additionally optionally include a process aid (i.e., viscosity reducing) plasticizer. In some desirable aspects, the triglyceride plasticizer is an epoxidized triglyceride plasticizer, and the process aid plasticizer is an ester plasticizer. The plasticizer components of the polymer 150 are typically liquid at room temperature (i.e., about 21° C.). It has been discovered herein that the weight ratio of triglyceride plasticizer to ester plasticizer can suitably fall within a prescribed weight ratio range of about 1:0 to about 3:2 to provide the desired viscoelastic, adhesive, cohesive, releasability, cleansability, and/or antimicrobial attributes for effective use herein. The content and type of plasticizers can have a pronounced effect upon imparting the desired inventive polymer 150 attributes herein. Thus, an appropriate balance within the cited range between the triglyceride plasticizer and ester plasticizer can provide an effective reaction media for preparing a thermoset viscoelastomeric polyurethane reaction product uniquely possessing the viscoelastic, adhesive, cohesive, releasability, cleansability, and antimicrobial compositional properties for the inventive viscoelastic materials 100 and inventive personal protective articles 110 of the present disclosure. Desirably, the plasticizer component is uniformly dispersed and cohesively bound throughout the thermosetting reaction media, along with the other polymerizable thermosetting components, and will tenaciously remain uniformly dispersed within the resultant polymer 150 in a highly cohesive, stabilized form (e.g., the plasticizer component will not leak from the polymer 150).

As referenced above, suitable triglyceride plasticizers for preparing the inventive polymer 150 can include epoxidized triglycerides. Epoxidized triglycerides such as the epoxidized animal and vegetable oils are especially effective as a plasticizer component in the thermosetting viscoelastomeric reaction media. Amongst the suitable triglyceride plasticizers, the epoxidized vegetable oils (e.g., soybean, castor, corn, cottonseed, perilla, safflower, linseed, tall, etc.) have been found to be highly effective triglyceride plasticizers herein. Such triglyceride plasticizers can be suitably present in an amount that is less than about 50 percent by weight of the polymer, such as from about 20 percent to about 50 percent by weight. In one example, epoxidized soybean oil can provide a suitable triglyceride plasticizer to form the inventive polymer 150 for use with the inventive viscoelastic materials 100 and inventive personal protective articles 110 of the present disclosure.

As referenced above, if present, suitable process aid (i.e., viscosity reducing) plasticizers for preparing the inventive polymer 150 can include ester plasticizers. Ester plasticizers, such as diester plasticizers, are especially effective as an additional plasticizer component in the thermosetting viscoelastomeric reaction media. Suitable ester plasticizers typically have a molecular weight of less than about 500, and can include the condensation products of alcohols (e.g., the $C_1$ to $C_{10}$ alcohols, such as the $C_2$-$C_6$ alcohols) and the dicarboxylic acids (e.g., the $C_2$-$C_{12}$ dicarboxylic acids, such as the $C_4$-$C_6$ dicarboxylic acids). In addition, amongst the more fluid ester plasticizers, such as diester plasticizers, are the lower dialkyl esters of dicarboxylic acids, such as dialkyl esters having alkyl groupings of less than 12 carbon atoms, more particularly the $C_1$-$C_5$ dialkyl ester grouping of sebacates, the adipates, the phathalates, the isophathalates, the maleates, the azelates, the gluterates, etc. which have been found to be highly effective ester plasticizers herein. Such ester plasticizers can be suitably present in an amount ranging from about 0 percent to about 40 percent by weight of the polymer, such as about 1 percent to about 20 percent by weight, or about 1 percent to about 10 percent by weight. In one example, dibutyl sebacate can provide a suitable ester plasticizer to form the inventive polymer 150 for use with the inventive viscoelastic materials 100 and inventive personal protective articles 110 of the present disclosure.

In some aspects, the incorporation (within the ranges set forth herein) of the relatively low molecular weight ester plasticizer (i.e., less than about 500) in combination with epoxidized triglyceride plasticizer can be utilized herein to provide an easier fabricating form (e.g., spraying, printing, etc.) of the uncured polymer mix by lowering its viscosity without adversely affecting its desirable thermoset properties. For example, the addition or substitution of the epoxidized triglycerides with polar ester plasticizers has been found to maintain a desired level of adhesiveness and cohesiveness while still retaining excellent releasability and stability properties. Polar ester plasticizers of a more fluid consistency at room temperature (i.e., about 21° C.) and typically of a relatively low molecular weight (e.g., less than about 500) can contribute to ideal working viscosities during the initial curing stages, rendering the coating of the polymer 150 onto and/or into the flexible substrate 170 component to be more effective.

The cross-linked polymeric structure of the thermoset polymerizate obtained from an appropriate thermoset reaction media provides an ideal infrastructure for effectively harboring plasticizer components in an unexpectedly superior adhesive and cohesive form, while also providing superior antimicrobial properties. Desirably, the plasticizer is uniformly incorporated throughout the reaction media containing the polymerizable components, and remains uniformly dispersed within the resultant polymer 150 in a highly cohesive form, thus preventing leakage of the plasticizers therefrom. It appears that the cross-linked infrastructure and the polarity provided by the polymerized polyether diols and polyether triols orients the polarized plasticizer components within the thermoset reaction product to impart the unexpected viscoelastic, adhesive, cohesive, releasability, cleansability, and antimicrobial properties to the polymer 150 herein. Thus, the thermosetting diols and triols in cooperative combination with the plasticizer create a thermoset polymeric structure possessing a high degree of compositional adhesiveness and cohesiveness for effective usage with the inventive viscoelastic materials 100 and inventive personal protective articles 110 of the present disclosure, while also allowing for a clean cohesive separation from a surface upon which the resulting polymer 150 comes into contact.

From a molecular infrastructure standpoint, the unique combination of cross-linking reactants and plasticizer types in the prescribed amounts creates a uniquely different polymer 150. The appropriate balance between diol and triol reactants appears to create long chain polarized sites ideal for powerful cohesive polar entrapment of the plasticizer while also aligning polarized plasticizer components in a powerful adhesive and cohesive positioning within the polymer 150. The polarized molecular alignment of the plasticizer cofactor within the polymer infrastructure contributes to a highly cohesive structure which maintains it molecular integrity when subjected to forces tending to cause separation of the polymer 150 from a contacting surface. The plasticizer appears also to be a major contributing factor in the polymer's unique viscoelastomeric properties. As a result, the polymer 150 possesses a host of unexpectedly unique and superior properties (e.g., adhesiveness, cohesiveness, releasability, cleansability, antimicrobial, etc.) over conventional polymer coatings of currently available on personal protective articles.

In addition, the thermosetting diols and triols in cooperative combination with the plasticizer create a polymer 150 having antimicrobial properties, as well as a thermoset viscoelastic polymeric structure possessing the high degree of compositional adhesiveness and cohesiveness necessary to adhesively secure and retain contaminants, while also allowing for a desired grip upon surfaces of an object upon which the polymer 150 comes into contact, as well as a clean cohesive separation from the surface. The type of plasticizers and reactants in monitored amounts can also be effectively utilized to provide desirable thermosetting fabricating conditions for preparing the polymer 150 component, and thereby providing inventive viscoelastic materials 100 and inventive personal protective articles 110 possessing the unique attributes herein.

The inventive adhesive and cohesive thermoset viscoelastic polymer 150 also possesses a tenacious internal compositional cohesiveness as evidenced by its ability to break cleanly away from a surface of an object upon which it comes into contact, substantially without leaving any residue of the polymer 150 remaining on the surface. In other words, although the inventive adhesive and cohesive thermoset viscoelastic polymer 150 herein generally possesses unexpectedly superior adhesiveness (which can be adjustable via reactant modification to a desired degree of adhesiveness), the polymer 150 also possesses unexpectedly superior cohesive release attributes. For example, upon exposure to a suitable adhesive separating release force (e.g. pulling an adhesively engaged footwear cover 112 away from a surface, such as flooring, upon which it has come into contact), the compositional cohesiveness of the polymer 150 will tenaciously retain its viscoelastic structural integrity by separating substantially cleanly from the surface upon which it has come into contact (i.e., without leaving more than a trace of polymeric residue upon the surface). Accordingly, upon adhesive separation from such surface, the polymer 150 will return to its substantially intact and innate form as when originally disposed upon the flexible substrate 170 component of the inventive viscoelastic materials 100, or inventive personal protective articles 110, leaving no more than a minuscule amount of the polymer 150 residue adhering to the surface, while still captively retaining contaminants from the separated surface. More typically, upon separation from a surface, there will exist no evidence of visible polymer 150 residue remaining upon the surface. It has been observed herein that the polymer 150 tends to pull away from a surface until the polymer 150 completely separates or breaks cleanly away from the surface, and then the polymer 150 forthrightly cohesively returns to its innate form as originally applied to the flexible substrate 170 component of the inventive viscoelastic materials 100, or inventive personal protective articles 110, of the present disclosure.

The extent of distortion exhibited by the polymer 150 upon exposure to separation forces from the surface of an object will depend largely upon the degree of adhesiveness of the polymer 150. It has been observed herein that, upon coming into contact with a surface of an object, the polymers 150 herein having relatively higher adhesiveness values will physically tend to tenaciously string-out similar to the pulling of heated candy taffy until a clean adhesive, but cohesive, separation ultimately occurs from the surface, whereupon the polymer 150 then returns to its original innate form, leaving substantially no residue upon the surface. It has also been observed herein that increasing the adhesiveness of the polymer 150 corresponds, on the one hand, to an increasing difficulty for the inventive viscoelastic materials 100 and inventive personal protective articles 110 of the present disclosure to release from an engaged surface (e.g., flooring, a tool, etc.), but also corresponds, on the other hand, to an increasing efficacy for removing contaminants from the surface.

Another benefit of the inventive viscoelastic materials 100 and inventive personal protective articles 110 of the present disclosure is that the viscoelastic, adhesive, cohesive, releasability, cleansability, and antimicrobial attributes of the inventive polymer 150 component can be tailored to meet the levels as desired for use of any particular material 100 or article 110. For example, footwear covers 112 designed for dust or microbe removal may employ a less adhesive polymer 150 than footwear covers 112 designed to remove more substantial contaminants such as dirt and debris. The overall tackiness and adhesiveness of the polymer 150 and its concomitant releasability characteristics may accordingly be effectively altered by changing the compositional makeup of the thermosetting reaction media, particularly via the diol to triol reaction media ratio, as well as the reaction media plasticizer content and type(s) of plasticizer. Thus, the adhesive and cohesive attributes of the resulting inventive polymer 150 can be tailored to meet a desired level of adhesiveness and cohesiveness for any given inventive viscoelastic material 100 and inventive personal protective articles 110 end usage. For example, the adhesiveness of the polymer 150 will tend to increase as the diol content increases (with respect to the triol content), and the adhesiveness of the polymer 150 will tend to decrease as the triol content increases (with respect to the diol content). Incidentally, it has been observed herein that for a given increase in the diol component content, it may be desirable to slightly increase the isocyanate prepolymer amount to generally balance the reaction media reactants.

Yet another benefit of the invention is that the adhesive and cohesive thermoset viscoelastic polymer 150 of the present disclosure can also be tailored for desired application processes onto the flexible substrate 170 component of the viscoelastic materials 100 and inventive personal protective articles 110. For example, the thermosetting reaction media used to form the polymer 150 will typically comprise liquid reactants at room temperature (i.e., about 21° C.). As a result, upon mixing, the viscosity characteristics of the resultant polymer mix in an uncured form can be effectively tailored so as to provide a workable viscosity for effectively forming the polymer onto and/or into the flexible substrate 170 component infrastructure. Accordingly, the thermosetting reaction media for preparing the polymer 150 may be characteristically formulated to possess desired coating viscosities and fluidity, such as for spraying, printing, film-forming, casting, molding, dipping, etc., during the initial formative thermosetting stages of the thermosetting reaction. Procedurally, in some aspects, a measured amount of the fluid uncured polymer mix may be coated upon a desired flexible substrate 170 and thereafter desirably cured to provide the desired polymer 150 component incorporated with the inventive viscoelastic materials 100 herein, or inventive personal protective articles 110. For example, upon applying the uncured polymer to the footwear covers 112 herein, a portion of the uncured polymer adsorbs onto and/or absorbs into the infrastructure of the flexible substrate 170 component, which will then, upon curing, tenaciously bond to the fibrous nonwoven flexible substrate 170 component of the footwear covers 112, such that the bonding force of the polymer 150 to the flexible substrate 170 of such personal protective articles 110 herein will be greater than the bonding force to a surface of an external object upon which the personal protective articles 110 come into contact. Indeed, controlling the initial viscosity properties of the uncured polymer mix provides a convenient manufacturing procedure for preforming the polymer 150 into a desired end product form. Thus, conventional spraying, printing, calendaring, casting, molding, dipping, etc. thermosetting coating techniques, at a workable viscosity range, can be effectively used to prepare the polymer 150 in a coating form, for example.

The viscosity of the thermosetting reaction media can be adjusted using various techniques, which can include, but is not limited to, varying the amount of plasticizer, varying the amount of diol, varying the amount of triol, varying the type and amount of catalyst, varying the temperature, and the like, as would be apparent to persons having ordinary skill in the art. For example, by adjusting the plasticizer content and type, the characteristics of the reaction media, including the ultimate thermoset adhesiveness, as well as the onset reaction media thermosetting viscosity characteristics, can be adjusted. Accordingly, the thermosetting reaction media can be thereby effectively altered so as to suit a particular type of manufacture. For example, one desirable method for adjusting the viscosity of the uncured polymer mix is to adjust the amount of process aid plasticizer (i.e., ester plasticizer). Indeed, such ester plasticizers, such as the diester plasticizers (e.g., dialkyl ester plasticizers, such as dibutyl sebacate), can have a profound effect on polymer viscosity. In general, as the amount of ester plasticizer increases, the viscosity of the uncured polymer decreases. Thus, the addition or substitution of a process aid plasticizer with the epoxidized triglyceride plasticizer component of the polymer formulation herein will generally impart sufficient onset fluidity reduction so as to provide an uncured polymer mix which can be easily sprayed, printed, poured, molded, casted, etc. in a desired coating form during its initial thermosetting stages, resulting in the formation of a tenacious bonding between the cured polymer 150 component and the flexible substrate 170 component of the inventive viscoelastic materials 100 and inventive personal protective articles 110 herein. Accordingly, in some aspects, the total ester plasticizer concentration in such application techniques can range from about 1 percent to about 40 percent by weight of the polymer, such as about 1 percent to about 20 percent by weight, or about 1 percent to about 10 percent by weight.

Polymeric components possessing viscoelastic, adhesive, cohesive, releasability, cleansability, and/or antimicrobial properties provide ideal inventive viscoelastic materials 100 and inventive personal protective articles 110, such as the footwear covers 112 described herein. Adhesive viscoelastomeric attributes of the inventive polymer 150 coupled with its inherent cohesiveness will allow the materials 100 and articles 110 to conform to the configuration of a surface upon which they come into contact, such as via pressure exerted upon them by a user, so as to effectively adhere to the surface and scavenge contaminants from the surface, even when the surface topography is variable, and to further cohesively entrain the contaminants upon cohesive release from such surface. The attributes of the polymer 150, as well as the varied suitable uses of the materials 100 and articles 110 herein, provide a wide latitude as to the particular form of the polymer 150 coating thereupon. Accordingly, the thickness of the polymer 150 may be adjusted to meet any desired application use. For example, coatings of the inventive polymer 150 measuring as little as 0.5 mm or less, or as much as 10 mm or more (as measured from the distal exterior surface of the polymer 150 to the exterior surface 132 of the flexible substrate 170), can retain their prefabricated structural cohesive integrity even when subjected to distorting opposing forces. For most coating applications of the polymer 150, a coating thickness ranging from about 0.1 mm to about 1 mm will suffice, although much thicker coatings (e.g., 3 mm, or 5 mm, or 10 mm, or greater) can be used without departing from the scope of the invention. In the case of footwear covers 112, for example, the adhesive attributes also allow it to provide a superior frictional grip (as compared to conventional footwear covers) upon a surface of which it comes into contact with a thickness as little as about 10 mm or less, such as from about 0.1 mm to about 10 mm, or about 0.5 mm to about 1 mm, which can provide enhanced safety and stability of the user, typically exhibiting a superior increase in coefficient of friction as compared to currently available footwear covers, yet also providing sufficient releasability attributes to prevent the footwear covers 112 from overly sticking to the surface and/or from the unintended removal of the footwear covers 112 from the user, in addition to removing contaminants from the surface, as well as imparting antimicrobial effects to the surface.

In addition, the thickness of the polymer 150 component can have a relatively consistent thickness profile, or the thickness profile can be relatively variable. For example, the manner in which the polymer 150 is incorporated and used as a component of the non-limiting exemplary personal protective articles 110 in the form of footwear covers 112 described herein will depend largely upon their intended end usage. For instance, in applications where a contact surface is relatively flat and/or smooth, the polymer 150 may be provided or incorporated within the footwear covers 112 as having a relatively thin and flat thickness profile to effectively provide sufficient grip and/or sufficiently remove contaminants as desired. Alternatively, where a contact surface topography is uneven, or in which contaminants may be hard to reach (e.g., a surface that is grooved, ridged, etc.), a comparatively thicker and/or less flat (i.e., more three-dimensional) and relatively variable polymer thickness profile may be preferred. Such a unique capacity to retrieve contaminants from difficult to reach areas arises because the polymer 150 possesses viscoelastomeric and adhesive properties. Consequently, upon application of pressure to the footwear covers 112 by a user, the polymer 150 will tend to viscoelastomerically conform to the topographical shape profile of the contact surface, and thereby improve grip while also effectively extracting contaminants therefrom. Upon release of pressure, and subsequent removal from the surface, the polymer 150 will return to its original innate form, carrying along the contaminants being adhesively retained thereto.

Typically, the fluid thermosetting reaction media constituents of the inventive adhesive and cohesive thermoset viscoelastic polymer 150 are mixed to form an uncured polymer mix (which typically initiates the curing process, although it may be formulated to require an initiator to start the curing process), and the polymer mix (while remaining in a substantially fluid form) is then applied or coated onto and/or at least partially into the infrastructure of the flexible substrate 170 component, and then allowed to fully cure to form the polymer 150 in a usable form, thus forming the inventive viscoelastic materials 100 or inventive personal protective articles 110 herein. In some aspects, it can be desirable that the thermosetting reaction media for forming the polymer 150 is directly bonded in situ onto and/or at least partially into the infrastructure of the flexible substrate 170 component. This can be accomplished, for example, by separately applying the reaction media constituents directly to the flexible substrate 170 component and thereafter initiating curing of the resulting polymer mixture in situ to provide a thermosetting polymer 150 bonded to the flexible substrate 170, which can form a more tenacious bonding to the flexible substrate 170 component than to any other surface upon which the polymer 150 later comes into contact. Similar to the more typical coating method described above, such in situ formation can allow for the cohesive removal of the footwear covers 112 from a given surface without the polymer 150 becoming detached from the footwear covers 112. In still other aspects, the polymer 150 can be preformed and cured prior to attachment to the flexible substrate 170 component, without departing from the scope of the invention. In such aspects, one or more preformed substrates of the polymer 150 can be attached to the flexible substrate 170 component via the adhesive forces of the polymer 150 itself and/or with additional suitable attachment means (e.g., stitching, ultrasonic, adhesives, etc.) as would be apparent to persons having ordinary skill in the art.

Referring now to FIG. 10, as referenced above, the adhesive and cohesive thermoset viscoelastic polymer 150 component of the inventive viscoelastic materials 100 and inventive personal protective articles 110 of the present disclosure can be effectively coated onto the flexible substrate 170 component via conventional thermosetting coating techniques, such as spraying, printing, calendaring, casting, molding, dipping, and the like, as would be apparent to persons having ordinary skill in the art. For example, in some desirable aspects, the polymer 150 can be applied utilizing a spraying system 200 technique. In one particular example, such a spraying system 200 can utilize an arrangement comprising the use of first and second metering pumps 203,204, each of which feed one component 201,202 of a two-part thermosetting reaction media solution through feed lines 205,206 to an application sprayer 207 comprising a mixing chamber 208 and a single spray nozzle 209, such as a 2.0 mm high-volume low-pressure (HVLP) paint sprayer nozzle available from Graco Minnesota Inc., having a place of business located in Minneapolis, Minn., USA. In such arrangement, the first metering pump 203 feeds a first solution 201 (e.g., Solution A) comprising an isocyanate prepolymer to the mixing chamber 208 of the application sprayer 207, and the second metering pump 204 feeds a second solution 202 (e.g., Solution B) comprising polyols, plasticizer and optionally other additives (e.g., initiator, catalyst, UV inhibitor/antioxidant, colorant, etc.) to the mixing chamber 208 of the application sprayer 207, each at suitable rates to form a mixture in the quantity ranges set forth herein. Accordingly, mixing of the two reaction media solutions 201,202 occurs in the mixing chamber 208 to form an uncured polymer mix 250. Upon mixing, the formed polymer mix 250 is then immediately forced through the nozzle 209, effecting spraying of polymer mix 250 onto a desired flexible substrate 170 component, and allowed to fully cure into the inventive polymer 150 herein, thus forming the inventive viscoelastic materials 100 and/or inventive personal protective articles 110 of the present disclosure. It should be understood that numerous other spraying equipment and configurations (e.g., HVLP paint sprayers, etc.) can also be utilized for the present invention, as would be apparent to persons having ordinary skill in the art, without departing from the scope of the invention. Similarly, other thermoset application techniques can also be utilized for the present invention, as would be apparent to persons having ordinary skill in the art, without departing from the scope of the invention.

The thermosetting reaction media constituents which form the inventive polymer 150 can be adjusted accordingly, as described above, to obtain a desired polymer mix viscosity upon mixing of the thermosetting solutions suitable for the spray system 200. Example viscosities for such a spray system arrangement can range from about 500 centipoise (cP) to about 8,000 cP, such as about 2,000 cP to about 3,000 cP. It should be understood that other desired viscosities can also be suitable depending on a variety of factors (e.g., spray system configuration, spray pressure, spray nozzle type and attributes, pattern of polymer application, thickness of polymer application, type of flexible substrate, desired soaking depth of polymer into the flexible substrate infrastructure, etc.), without departing from the scope of the invention.

In addition, the spray system 200 utilizes pressure to force the polymer mix through the spray nozzle 209. Example spray pressures for such a spray system 200 arrangement can range from about 50 pounds per square inch (psi) to about 150 psi (345 kPa-1,034 kPa). It should be understood that other desired pressures can also be utilized depending on a variety of factors (e.g., spray system configuration, polymer viscosity, spray nozzle type and attributes, pattern of polymer application, thickness of polymer application, desired spray drop size, type of flexible substrate, desired soaking depth of polymer into the flexible substrate infrastructure, etc.), without departing from the scope of the invention.

Although the thermosetting reaction media constituents can be applied by a variety of application techniques, application by spraying the polymer mix at a sprayable viscosity onto a suitable flexible substrate 170 component has been found to be highly effective. In spray applications, the viscosity of the polymer mix will typically be adjusted to a higher viscosity range than normally used in most paint spray applications. Through proper spray volume, nozzle selection and pressure, the spray application may effectively spray a globular droplet of polymer mix onto the substrate 170 structure which can tangentially attach to the substrate structure and remain thereupon while penetrating and impregnating onto the interior subsurface regions thereof. Factors affecting this tangential embedding of the contacting thermosetting droplet can include the droplet viscosity, the extent of cross-linking, the droplet form, size and the pressure of application, the type and amount of catalyst, the reaction temperature, and the like, as would be apparent to persons having ordinary skill in the art. In some aspects, it may be desirable that the applied droplet viscosity is sufficient to maintain droplet configuration for a period of time to permit sufficient droplets to be selectively absorbed and embedded within the flexible substrate 170 solid structure. In some aspects, if the polymer mix becomes prematurely excessively cross-linked, the premature cross-linked polymer mix can adversely affect absorption, anchoring and uniform embedding of the polymer 150 into the substrate structure, which could result in undesirable detachment of the polymer 150 from an inventive viscoelastic material 100 or inventive personal protective article 110 when attempting to release from an object upon which it has come into contact.

Referring now to FIGS. 1A-2B, 4C and 7A-7D, in some aspects, the polymer 150 coating can be applied to the flexible substrate 170 component of the inventive viscoelastic materials 100 and inventive personal protective articles 110 of the present disclosure in a relatively continuous application. In other aspects, the polymer 150 coating can be applied in a pattern. FIGS. 7A-7D illustrate several non-limiting exemplary patterns which can be suitable for the present invention. It should be understood that numerous other patterns can also be suitable for present invention as would be apparent to persons having ordinary skill in the art without departing from the scope of the invention.

In some aspects, such as in the case of footwear covers 112 for example, to obtain enhanced traction between the interior surface 134 of the main body 120 and the sole (not shown) of either the user's foot or shoe (not shown), a polymer 150 coating may optionally also be applied to the interior surface 134 of panels 122 and/or 124, such as near the bottom portion 129 thereof, without departing from the scope of the invention. The polymer coating (not shown) applied to the interior surface 134 may have a relatively continuous profile, or may be applied as a pattern, similar to or different than the patterns applied to the exterior surface 132 of the personal protective articles 110.

It has been unexpectedly discovered herein that by at least partially coating the flexible substrate 170 component of the inventive viscoelastic materials 100 and/or inventive personal protective articles 110 herein with the unique adhesive and cohesive thermoset viscoelastic polymer 150, the materials 100 and articles 110 can provide a host of unique properties. For example, unlike conventional footwear covers that have currently available traction enhancing substances coated onto the bottom sides thereof, which primarily only marginally increase the coefficient of friction of surfaces upon which they come into contact, and furthermore which are not equivalently adhesive to the inventive footwear covers 112 herein and are not antimicrobial, and moreover which typically cannot be laundered and re-used, it has been found that the inventive adhesive and cohesive thermoset viscoelastic polymer 150 of the present invention will create unique viscoelastic, adhesive, cohesive, releasability, cleansability, and antimicrobial properties for the footwear cover 112 use, providing a tenacious adhesiveness for a superior coefficient of friction, providing effective removal of adverse contaminants from both the surfaces of objects and the surrounding environment, providing removal of the footwear covers 112 from surfaces substantially without leaving polymer residue, imparting antimicrobial effects to the surfaces, and providing for laundering and re-use of the footwear covers 112. Such unique attributes provide for viscoelastic materials 100 and personal protective articles 110 which are far superior to currently available equivalent substrates and personal protective articles.

A unique attribute of the inventive viscoelastic materials 100 and inventive personal protective articles 110 of the present disclosure equipped with the adhesive and cohesive thermoset viscoelastic polymer 150 herein includes, inter alio, an ability to remove contaminants that are adhesively engaged to the polymer 150 (e.g., after a use) simply via conventional washing and/or other such contaminant removal techniques. For example, unlike conventional footwear covers which must be discarded after merely a single use, the polymer 150 equipped footwear covers 112 of the present invention may be cleansed from contaminants and restored to their original adhesive, cohesive and antimicrobial efficacy. Surprisingly, conventional washing (e.g., hand-washing, scrubbing, washing machines, dishwashers, etc.) or autoclaving may be effectively utilized to eradicate and remove contaminants therefrom and thereby permit fully functional reuse of the cleansed footwear covers 112. Accordingly, the footwear covers 112 of the present invention are equipped with exposed regions composed of the inventive polymer 150 adapted to adhesively remove contaminants from the surfaces of objects upon which they come into contact, as well as potentially from the surrounding environment (e.g., airborne contaminants), and thereafter cohesively release the contaminants therefrom upon cleansing.

Other uses for the inventive viscoelastic materials 100 and inventive personal protective articles 110 of the present disclosure embrace a broad range of hygienic, medical and cleanroom uses. Accordingly, medical and dental clinics, hospitals, surgical operating sites, elderly care sites, and a host of other hygienic uses would greatly benefit from the ability to adhesively restrain and inhibit pathogenic invasion from outside sources. Similarly, business establishments, manufacturing facilities, electronics manufacturing, public premises, arenas, schools, spas, swimming pools, food processing plants, restaurants, cafeterias, showering sites, bathrooms, and a host of other uses would likewise greatly benefit from the adhesive, cohesive, releasable, cleansable, antimicrobial, and reusable materials 100 and articles 110 of the present invention.

Referring now to FIG. 8, in some aspects, it may be desirable to include a protective release substrate 160 (i.e., a releasable covering) disposed upon the exposed polymer 150 coated onto the flexible substrate 170 component of the inventive viscoelastic materials 100 and inventive personal protective articles 110 of the present disclosure, such as prior to initial use (such as when within a packaging, for example). Since the polymer 150 has a propensity to adhere to items upon which it comes into contact before being placed into operational use, such a protective release substrate 160 can be disposed upon the polymer 150 component to protect the integrity of the polymer 150 component, as well as the integrity of objects and surface upon which the polymer 150 would otherwise potentially come into contact. Such a protective release substrate 160 can then be removed or peeled away at the time of use to thereby expose the uncontaminated surface of the polymer 150 component for operational use. A suitable protective release substrate 160 can desirably comprise a substance that exhibits a relatively low adhesiveness when mated to the inventive polymer 150 component, including, but not limited to, certain plastic films (e.g., PVC), waxed papers (e.g., paraffin wax), TEFLON, and the like.

The invention herein also includes methods for manufacturing the inventive viscoelastic materials 100 and personal protective articles 110 herein. One such method comprises the following:

1. providing a flexible substrate 170;
2. providing a thermosetting reaction media comprising:
   a. about 4 wt % to about 8 wt % isocyanate prepolymer (e.g., a polyol reacted with an isocyanate), preferably a diisocyanate prepolymer (e.g., methylene diphenyl diisocyanate (MDI));
   b. about 35 wt % to about 55 wt % polyols comprising:
      i. about 0 wt % to about 20 wt % polyether diol, and
      ii. about 10 wt % to about 50 wt % polyether triol; and
   c. about 20 wt % to about 60 wt % plasticizer comprising:
      i. about 20 wt % to about 50 wt % of an epoxidized triglyceride plasticizer (e.g., epoxidized vegetable oil, such as epoxidized soybean oil), and
      ii. about 0 wt % to about 40 wt % of an ester plasticizer (e.g., a diester plasticizer, such as a dialkyl ester plasticizer, such as dibutyl sebacate);

3. mixing the thermosetting reaction media to form a polymer mix;
4. applying the polymer mix onto the flexible substrate 170 to form a polymer mix coating;
5. allowing the polymer mix coating to fully cure to form an adhesive and cohesive thermoset viscoelastic polymer 150 disposed upon the flexible substrate, thus forming an inventive viscoelastic material 100 of the present invention; and
6. optionally fabricating a personal protective article from the viscoelastic material 100 of step 5 to form an inventive adhesive and cohesive personal protective article 110 of the present disclosure.

Another method comprises the following:
1. providing a personal protective article comprising a flexible substrate 170;
2. providing a thermosetting reaction media comprising:
   a. about 4 wt % to about 8 wt % isocyanate prepolymer (e.g., a polyol reacted with an isocyanate), preferably a diisocyanate prepolymer (e.g., methylene diphenyl diisocyanate (MDI));
   b. about 35 wt % to about 55 wt % polyols comprising:
      i. about 0 wt % to about 20 wt % polyether diol, and
      ii. about 10 wt % to about 50 wt % polyether triol; and
   c. about 20 wt % to about 60 wt % plasticizer comprising:
      i. about 20 wt % to about 50 wt % of an epoxidized triglyceride plasticizer (e.g., epoxidized vegetable oil, such as epoxidized soybean oil), and
      ii. about 0 wt % to about 40 wt % of an ester plasticizer (e.g., a diester plasticizer, such as a dialkyl ester plasticizer, such as dibutyl sebacate);
3. mixing the thermosetting reaction media to form a polymer mix;
4. applying the polymer mix onto the flexible substrate 170 component of the personal protective article to form a polymer mix coating;
5. allowing the polymer mix coating to fully cure to form an adhesive and cohesive thermoset viscoelastic polymer 150 disposed upon the personal protective article, thus forming an inventive adhesive and cohesive personal protective article 110 of the present disclosure.

The present invention may be better understood with reference to the following examples.

EXAMPLES

Example 1

A thermoset viscoelastic reaction product adapted to provide an inventive thermoset viscoelastic polymer 150 of the present invention having exceptional viscoelastic, adhesive, cohesive, releasability, cleansability, and antimicrobial efficacy was prepared by uniformly admixing together a two-part thermosetting reaction media mix comprising Solution A and Solution B, as follows:

Solution A—Solution A contained 10 parts of 4,4'-methylenediphenyl diisocyanate (MDI) based glycol prepolymer (ELASTOCAST TQZ-P23, available from BASF Corporation);

Solution B—Solution B was prepared by combining 17.2 parts of 2 functional polyether diol (ELASTOCAST C4057, available from BASF Corporation), 51.4 parts of 3 functional polyether triol (ELASTOCAST C4018, available from BASF Corporation), 70.0 parts of epoxidized soybean oil plasticizer, 7.5 parts of dibutyl sebacate plasticizer, 0.5 parts of a bismuth-based catalyst (COSCAT 83, available from Vertellus Holdings LLC, having a place of business located in Zeeland, Mich., USA), 3.2 parts of a UV stabilizer (comprising UV inhibitor and antioxidant) (TINUVIN B 75, available from BASF Corporation), and 1.5 parts of a colorant.

Solution A and Solution B were then each separately pumped at suitable rates via metering pumps to a single spray canister and nozzle system where the solutions were combined and mixed to form an uncured polymer mix comprising about 6.2 percent by weight Solution A and about 93.8 percent by weight Solution B. Upon mixing of Solution A with Solution B in the canister, the curing process was initiated. The polymer mix was then immediately forced through the nozzle and subsequently sprayed onto a surface of a nonwoven flexible substrate until a coating thickness of about 1 mm of the polymer mix was obtained. The polymer mix coating was then allowed to cure for 24 hours until completely cured to form an inventive adhesive and cohesive thermoset viscoelastic polymer 150 of the present disclosure. Accordingly, the polymer 150 combined with the flexible substrate 170 provided an inventive viscoelastic material 100 of the present invention, which could suitably be fabricated into a personal protective article 110 (e.g., a footwear cover 112).

Example 2

The adhesive and cohesive thermoset viscoelastic polymer 150 side of an inventive viscoelastic material 100 formed in accordance with Example 1 was pressed onto a lab counter top using a hand pressure of about 5 pounds (2.3 kg). It was observed that the viscoelastic material 100 provided excellent grip with respect to the counter top surface. The viscoelastic material 100 was then subsequently removed (i.e., peeled away) from the counter top. It was observed that the viscoelastic material 100 released from the counter top with relatively little effort. The counter top was then inspected, which revealed that no polymer 150 residue was visually observed to have been deposited or remained thereupon. In addition, the polymer 150 located on the viscoelastic material 100 was inspected, which revealed that the polymer 150 coating remained intact (i.e., appeared to be visually similar in structure and topography to the coating prior to contact), and furthermore had a relatively light coating of contaminants (predominantly dust and lint) adhered thereto. The contaminated viscoelastic material 100 was then hand-washed in a sink using a combination of dish soap (DAWN dish detergent, available from Proctor & Gamble Co., having a place of business located in Cincinnati, Ohio, USA) and tap water. The cleansed viscoelastic material 100 was then rinsed with tap water (to remove any residual contaminants and detergent), and then allowed to fully dry at room temperature (i.e. about 21° C.). Upon drying, the viscoelastic material 100 was again inspected, which revealed that the contaminants had been substantially completely removed, that the polymer 150 coating remained intact in its original innate form, and that the polymer 150 retained its original tackiness (i.e., adhesiveness), as compared to the tackiness prior to use.

Example 3

The adhesive and cohesive thermoset viscoelastic polymer 150 side of an inventive viscoelastic material 100 formed in accordance with Example 1 was placed onto a tiled flooring and then stepped upon by a user, exerting a mass of about 180 pounds (82 kg) thereupon. It was observed that the viscoelastic material 100 provided excellent grip with respect to the flooring surface, and appeared to conform to the uneven topographical profile of the tiled flooring surface. The viscoelastic material 100 was then subsequently removed (i.e., peeled away by hand) from the flooring surface. It was observed that the viscoelastic material 100 released from the flooring surface with relatively little effort, exhibiting an adhesiveness release that felt relatively equivalent to that of Example 2. The flooring surface was then inspected, which revealed a visually cleaner area where the polymer 150 had come into contact, and that no polymer 150 residue was visually observed to have been deposited or remained thereupon. In addition, the polymer 150 located on the viscoelastic material 100 was inspected, which revealed that the polymer 150 coating remained intact (i.e., appeared to be visually similar in structure and topography to the coating prior to contact), and furthermore had a more pronounced covering (as compared to Example 2) of contaminants (predominantly dust, dirt and debris) adhered thereto. The contaminated viscoelastic material 100 was then hand-washed in a sink using a combination of dish soap (DAWN dish detergent) and tap water. The cleansed viscoelastic material 100 was then rinsed with tap water (to remove any residual contaminants and detergent), and then allowed to fully dry at room temperature (i.e. about 21° C.). Upon drying, the viscoelastic material 100 was again inspected, which revealed that the contaminants had been substantially completely removed, that the polymer 150 coating remained intact in its original innate form, and that the polymer 150 retained its original tackiness (i.e., adhesiveness), as compared to the tackiness prior to use.

It will be appreciated that details of the foregoing examples, given for purposes of illustration, are not to be construed as limiting the scope of the present invention. Although only a few exemplary embodiments of the present invention have been described in detail above, persons having skill in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of the present invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. A viscoelastic material comprising a flexible substrate and an adhesive and cohesive thermoset viscoelastic polymer, wherein the adhesive and cohesive thermoset viscoelastic polymer comprises:
    A. about 4 wt % to about 8 wt % isocyanate prepolymer;
    B. about 35 wt % to about 55 wt % polyols having repetitive ether groups; and
    C. about 20 wt % to about 60 wt % plasticizer;
    wherein the polyols comprise 0 wt % to about 20 wt % straight chain linking diols by weight of the polymer and about 10 wt % to about 50 wt % cross-linking triols by weight of the polymer;
    wherein the plasticizer comprises less than 45 wt % triglyceride plasticizer by weight of the polymer;
    wherein the adhesive and cohesive thermoset viscoelastic polymer prevents plasticizer leakage; and
    wherein the adhesive and cohesive thermoset viscoelastic polymer leaves substantially no residue upon its release from a surface upon which it comes into contact.

2. The viscoelastic material of claim 1 wherein the isocyanate prepolymer is a diisocyanate prepolymer.

3. The viscoelastic material of claim 2 wherein the diisocyanate prepolymer comprises methylene diphenyl diisocyanate.

4. The viscoelastic material of claim 1 wherein the straight chain linking diols are present in an amount of about 5 wt % to about 15 wt % by weight of the polymer and the cross-linking triols are present in an amount of about 20 wt % to about 40 wt % by weight of the polymer.

5. The viscoelastic material of claim 1 wherein the straight chain linking diols and cross-linking triols each have a molecular weight ranging from about 1,000 to about 10,000.

6. The viscoelastic material of claim 1 further comprising a straight chain linking diols to cross-linking triols weight ratio of 0:1 to about 1:1.

7. The viscoelastic material of claim 1 wherein the straight chain linking diols comprise polyether diol and the cross-linking triols comprise polyether triol.

8. The viscoelastic material of claim 1 wherein the plasticizer comprises:
    A. about 20 wt % to less than 45 wt % triglyceride plasticizer by weight of the polymer; and
    B. 0 wt % to about 40 wt % ester plasticizer by weight of the polymer.

9. The viscoelastic material of claim 8 further comprising a triglyceride plasticizer to ester plasticizer weight ratio of about 1:0 to about 3:2.

10. The viscoelastic material of claim 8 wherein the triglyceride plasticizer comprises an epoxidized triglyceride plasticizer and the ester plasticizer comprises a diester plasticizer.

11. The viscoelastic material of claim 10 wherein the epoxidized triglyceride plasticizer comprises epoxidized vegetable oil and the diester plasticizer comprises dialkyl ester plasticizer.

12. The viscoelastic material of claim 11 wherein the epoxidized vegetable oil comprises epoxidized soybean oil and the dialkyl ester plasticizer comprises dibutyl sebacate.

13. The viscoelastic material of claim 1 wherein the adhesive and cohesive thermoset viscoelastic polymer is at least partially disposed upon a surface of the flexible substrate in the form of a coating.

14. The viscoelastic material of claim 13 wherein the coating has a thickness of about 0.1 mm to about 10 mm.

15. The viscoelastic material of claim 1 further comprising at least one additive selected from initiators, catalysts, UV inhibitors, antioxidants and colorants.

16. The viscoelastic material of claim 1 wherein the viscoelastic material exhibits viscoelastic, adhesive, cohesive, releasability, cleansability and antimicrobial properties.

17. The viscoelastic material of claim 1 wherein the viscoelastic material is in the form of a personal protective article.

18. The viscoelastic material of claim 17 wherein the personal protective article is selected from footwear covers, surgical gowns, surgical drapes, gloves, hats, facemasks, coveralls, body suits, mats, pads, and aprons.

19. The viscoelastic material of claim 18 wherein the personal protective article is in the form of a footwear cover.

20. The viscoelastic material of claim 17 wherein the flexible substrate of the viscoelastic material is selected from nonwoven fabrics, woven fabrics, rubbers, nitrile, foams, leather, flexible plastics, or combinations thereof.

21. A footwear cover comprising a viscoelastic material, wherein the viscoelastic material comprises an adhesive and cohesive thermoset viscoelastic polymer coated onto a flexible substrate;
   wherein the flexible substrate comprises a nonwoven fabric;
   wherein the adhesive and cohesive thermoset viscoelastic polymer comprises:
      A. about 4 wt % to about 8 wt % methylene diphenyl diisocyanate prepolymer;
      B. 0 wt % to about 20 wt % polyether diol;
      C. about 10 wt % to about 50 wt % polyether triol;
      D. about 20 wt % to less than 45 wt % epoxidized soybean oil; and
      E. 0 wt % to about 40 wt % dibutyl sebacate;
   wherein the adhesive and cohesive thermoset viscoelastic polymer prevents plasticizer leakage; and
   wherein the adhesive and cohesive thermoset viscoelastic polymer leaves substantially no residue upon its release from a surface upon which it comes into contact.

22. The footwear cover of claim 21 further comprising a polyether diol to polyether triol weight ratio of 0:1 to about 1:1 and an epoxidized soybean oil to dibutyl sebacate weight ratio of about 1:0 to about 3:2.

23. The footwear cover of claim 21 wherein the adhesive and cohesive thermoset viscoelastic polymer coated onto the flexible substrate is configured as a pattern.

24. The footwear cover of claim 21 wherein the footwear cover exhibits viscoelastic, adhesive, cohesive, releasability, cleansability and antimicrobial properties.

25. A method for making a viscoelastic material comprising:
   A. providing a flexible substrate;
   B. providing a thermosetting reaction media comprising:
      i. about 4 wt % to about 8 wt % diisocyanate prepolymer;
      ii. about 35 wt % to about 55 wt % polyols comprising:
         a) 0 wt % to about 20 wt % polyether diol by weight of the reaction media, and
         b) about 10 wt % to about 50 wt % polyether triol by weight of the reaction media; and
      iii. about 20 wt % to about 60 wt % plasticizer comprising:
         a) about 20 wt % to less than 45 wt % epoxidized triglyceride plasticizer by weight of the reaction media; and
         b) 0 wt % to about 40 wt % dialkyl ester plasticizer by weight of the reaction media;
   C. mixing the thermosetting reaction media to form a polymer mix;
   D. applying the polymer mix onto the flexible substrate to form a polymer mix coating; and
   E. allowing the polymer mix coating to fully cure to form an adhesive and cohesive thermoset viscoelastic polymer;
   wherein the adhesive and cohesive thermoset viscoelastic polymer prevents plasticizer leakage; and
   wherein the adhesive and cohesive thermoset viscoelastic polymer leaves substantially no residue upon its release from a surface upon which it comes into contact.

26. The method of claim 25 further comprising fabricating the viscoelastic material into a personal protective article.

27. The method of claim 25 wherein the diisocyanate prepolymer is a methylene diphenyl diisocyanate-based prepolymer, the epoxidized triglyceride plasticizer is epoxidized soybean oil, and the dialkyl ester plasticizer is dibutyl sebacate.

28. The method of claim 25 wherein the thermosetting reaction media further comprises a polyether diol to polyether triol weight ratio of 0:1 to about 1:1 and an epoxidized triglyceride plasticizer to dialkyl ester plasticizer weight ratio of about 1:0 to about 3:2.

29. A method for making an adhesive and cohesive personal protective article comprising:
   A. providing an uncoated personal protective article comprising a flexible substrate;
   B. providing a thermosetting reaction media comprising:
      i. about 4 wt % to about 8 wt % diisocyanate prepolymer;
      ii. about 35 wt % to about 55 wt % polyols comprising:
         a) 0 wt % to about 20 wt % polyether diol by weight of the reaction media, and
         b) about 10 wt % to about 50 wt % polyether triol by weight of the reaction media; and
      iii. about 20 wt % to about 60 wt % plasticizer comprising:
         a) about 20 wt % to less than 45 wt % epoxidized vegetable oil by weight of the reaction media; and
         b) 0 wt % to about 40 wt % dialkyl ester plasticizer by weight of the reaction media;
   C. mixing the thermosetting reaction media to form a polymer mix;
   D. applying the polymer mix onto the flexible substrate of the uncoated personal protective article to form a polymer mix coating; and
   E. allowing the polymer mix coating to fully cure to form an adhesive and cohesive thermoset viscoelastic polymer;
   wherein the adhesive and cohesive thermoset viscoelastic polymer prevents plasticizer leakage; and
   wherein the adhesive and cohesive thermoset viscoelastic polymer leaves substantially no residue upon its release from a surface upon which it comes into contact.

30. The method of claim 29 wherein the diisocyanate prepolymer is a methylene diphenyl diisocyanate-based prepolymer, the epoxidized vegetable oil plasticizer is epoxidized soybean oil, and the dialkyl ester plasticizer is dibutyl sebacate.

31. The method of claim 29 wherein the thermosetting reaction media further comprises a polyether diol to polyether triol weight ratio of 0:1 to about 1:1 and an epoxidized vegetable oil plasticizer to dialkyl ester plasticizer weight ratio of about 1:0 to about 3:2.

* * * * *